United States Patent [19]

Renner et al.

[11] 4,444,768

[45] Apr. 24, 1984

[54] PYRIMIDO[1,6-A]INDOLES, PHARMACEUTICAL PREPARATIONS CONTAINING THEM, AND METHODS OF TREATING PAIN AND INFLAMMATION WITH THEM

[75] Inventors: Ulrich Renner, Riehen; Knut A. Jaeggi, Basel, both of Switzerland

[73] Assignee: Ciba-Geigy Corporation, Ardsley, N.Y.

[21] Appl. No.: 394,369

[22] Filed: Jul. 1, 1982

Related U.S. Application Data

[63] Continuation-in-part of Ser. No. 239,720, Mar. 2, 1981, abandoned.

[30] Foreign Application Priority Data

Mar. 4, 1980 [CH] Switzerland .................. 1703/80
Aug. 3, 1981 [CH] Switzerland .................. 5004/81

[51] Int. Cl.$^3$ .................. A61K 31/505; C07D 487/04
[52] U.S. Cl. .................. 424/246; 424/248.57; 424/251; 544/60; 544/115; 544/252
[58] Field of Search .................. 424/251, 248.57, 246; 544/252, 60, 115

[56] References Cited

U.S. PATENT DOCUMENTS

| | | | |
|---|---|---|---|
| 3,635,966 | 1/1972 | Duncan, Jr. .................. | 544/246 X |
| 3,814,759 | 6/1974 | Wei .................. | 544/250 |
| 3,887,566 | 6/1975 | Rodway et al. .................. | 544/233 X |
| 4,112,098 | 9/1978 | Vogt .................. | 544/250 X |
| 4,256,748 | 3/1981 | Chodnekar et al. .................. | 424/251 |
| 4,307,234 | 12/1981 | Jirovsky .................. | 544/247 |

FOREIGN PATENT DOCUMENTS

| | | |
|---|---|---|
| 8950 | 3/1980 | European Pat. Off. . |
| 35474 | 9/1981 | European Pat. Off. . |

OTHER PUBLICATIONS

Borisova, et al., Chemical Abstracts, vol. 86, 89748w (1977).
Nagai, et al., Chemical Abstracts, vol. 92, 58536v (1980).
Gadaginmath, et al., Indian Journal of Chemistry, vol. 13, pp. 1247-1250 (1975).
Borisova, et al., Chemical Abstract, vol. 74, 22729z (1971).
Cohen, et al., Chemical Abstracts, vol. 75, 76387e (1971).
Bhandari, et al., Chemical Abstracts, vol. 75, 110202y (1971).
Borisova, et al., Chemical Abstracts, vol 77, 139850k (1972).
Gadaginmath, et al., Chemical Abstracts, vol. 83, 141748a (1975).
Artemenko, et al., Chemical Abstracts, vol. 86, 37493q (1977).

Primary Examiner—Donald G. Daus
Assistant Examiner—Diana G. Rivers
Attorney, Agent, or Firm—Irving N. Feit

[57] ABSTRACT

Novel amidines, especially N,N'-bridged carboxylic acid amidines of the general formula

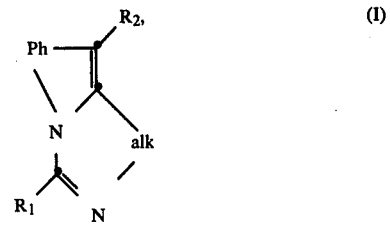

in which $R_1$ represents an aromatic radical, $R_2$ represents optionally esterified or amidated 1-carboxy-lower alkyl, Ph represents optionally substituted 1,2-phenylene and alk represents an aliphatic hydrocarbon radical separating the imino group from the methine group by from 1 to 3 carbon atoms, and their salts, have, inter alia, anti-inflammatory activity and can be used as active medicament substances in pharmaceutical preparations. They are produced according to methods known per se.

47 Claims, No Drawings

PYRIMIDO[1,6-A]INDOLES, PHARMACEUTICAL PREPARATIONS CONTAINING THEM, AND METHODS OF TREATING PAIN AND INFLAMMATION WITH THEM

This is a continuation-in-part of application Ser. No. 239,720, filed Mar. 2, 1981.

The invention relates to novel amidines, especially N,N'-bridged carboxylic acid amidines of the general formula

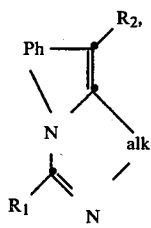

in which
$R_1$ represents an aromatic radical,
$R_2$ represents optionally esterified or amidated 1-carboxy-lower alkyl,
Ph represents optionally substituted 1,2-phenylene, and
alk represents an aliphatic hydrocarbon radical separating the imino group from the methine group by from 1 to 3 carbon atoms, their salts, processes for their manufacture, pharmaceutical preparations containing them and their use as an active substance in medicaments.

An aromatic radical can be carbocyclic or heterocyclic and substituted and is, for example, phenyl optionally substituted by lower alkyl, by lower alkoxy, by optionally halogen-containing lower alkylthio, lower alkanesulphinyl or lower alkanesulphonyl, by optionally substituted sulphamoyl, and/or by halogen, or heteroaryl optionally substituted, for example, by lower alkyl, lower alkoxy and/or halogen. Substituted sulphamoyl is, for example, N-mono- or N,N-di-lower alkylsulphamoyl.

Heteroaryl is, for example, monocyclic, preferably 5- or 6-membered heteroaryl and contains as hetero atom nitrogen, oxygen or sulphur, or nitrogen and, in addition, sulphur or oxygen. 5-membered radicals of this type are, for example, pyrrolyl, such as 2-pyrrolyl, furyl, such as 2-furyl, thienyl, such as 2- or 3-thienyl, or thiazolyl, such as 2-thiazolyl. 6-membered heteroaryl contains at least one nitrogen atom and is, for example, pyridyl, such as 2-, 3- or 4-pyridyl, or pyrimidyl, such as 2-pyrimidyl.

Esterified 1-carboxy-lower alkyl contains as esterified carboxy group, for example lower alkoxycarbonyl, which may also be substituted once by optionally substituted aryl, such as phenyl or pyridyl, or one or more times by hydroxy, halogen or lower alkoxy, such as lower alkoxycarbonyl optionally substituted by hydroxy, lower alkoxy and/or halogen, for example mono- or di-hydroxy-lower alkoxy, halogen- or lower alkoxy-lower alkoxycarbonyl, or phenyl-lower alkoxycarbonyl substituted by lower alkyl, lower alkoxy and/or halogen.

Amidated 1-carboxy-lower alkyl contains as amidated carboxy group, for example carbamoyl, which may optionally be substituted once by hydroxy or amino, once or twice by lower alkyl or hydroxy-lower alkyl, or twice by 4- to 7-membered lower alkylene or 3-oxa-, 3-thia- or 3-aza-alkylene. The following may be mentioned as examples: N-hydroxy-, N-amino-, N-mono- or N,N-di-lower alkyl-, or N-mono- or N,N-di-hydroxyalkylcarbamoyl. Carbamoyl N-substituted twice by 4- to 7-membered lower alkylene is, for example, pyrrolidino- or piperidino-carbonyl, or morpholino-, thiomorpholino-, piperazine- or N-lower alkylpiperazino-, such as N-methylpiperazino-, carbonyl.

1,2-phenylene is optionally additionally substituted one or more times, for example by lower alkyl, lower alkoxy, halogen or trifluoromethyl.

The radical alk is, for example, a lower alkylene radical separating the methine group from the imino group by from 1 to 3 carbon atoms, such as ethylene, 1,2- or especially 1,3-propylene, or is a vinylene radical separating the methine group from the imino group by 2 carbon atoms.

In the present description, by organic radicals and compounds referred to as "lower" there are preferably to be understood those having up to and including 7, especially up to and including 4, carbon atoms.

The general definitions used hereinbefore and hereinafter have, within the scope of the present description, especially the following meanings:

Lower alkyl is, for example, methyl, ethyl, n-propyl, isopropyl, n-butyl, isobutyl, sec.-butyl, tert.-butyl, and also a pentyl, hexyl or heptyl radical.

Lower alkoxy is, for example, methoxy, ethoxy, n-propoxy, isopropoxy, n-butoxy, isobutoxy, sec.-butoxy or tert.-butoxy.

Lower alkylthio is, for example, methylthio, ethylthio, n-propylthio, isopropylthio, n-butylthio, isobutylthio, sec.-butylthio, tert.-butylthio, n-pentylthio, n-hexylthio or n-heptylthio, and lower alkanesulphinyl or -sulphonyl is, for example, methane-, ethane- or n-propanesulphinyl or -sulphonyl.

N-lower alkylsulphamoyl, is, for example, N-methylsulphamoyl, N-ethylsulphamoyl or N-propylsulphamoyl, and N,N-di-lower alkylsulphamoyl is, for example, N,N-dimethylsulphamoyl, N,N-diethylsulphamoyl, N,N-methylethylsulphamoyl or N,N-dipropylsulphamoyl.

Halogen is, for example, halogen having up to and including an atomic number of 35, such as fluorine, chlorine or bromine.

Halo-lower alkylthio is, for example, chloromethylthio, chloroethylthio or chloropropylthio or one of the corresponding fluoro- or bromo-lower alkylthio groups.

Halo-lower alkanesulphinyl or -sulphonyl is, for example, chloromethane-, chloroethane- or chloropropanesulphinyl or -sulphonyl and the corresponding fluoro- or bromo-lower alkanesulphinyl or -lower alkanesulphonyl groups.

Lower alkoxycarbonyl is, for example, methoxycarbonyl, ethoxycarbonyl, n-propoxycarbonyl, butoxycarbonyl, or a pentyloxycarbonyl, hexyloxycarbonyl or heptyloxycarbonyl radical.

Phenyl- and pyridyl-lower alkoxycarbonyl are, for example, phenylmethoxycarbonyl, phenylethoxycarbonyl and 2-, 3- or 4-pyridylmethoxycarbonyl respectively.

Hydroxy-lower alkoxycarbonyl is, for example, 1- or 2-hydroxyethylcarbonyl, 1- or 3-hydroxypropylcarbonyl or 1- or 4-hydroxybutylcarbonyl and dihydroxy-lower alkoxycarbonyl is, for example, 2,3-dihydroxypropoxycarbonyl, 2,3-, 2,4- or 3,4-dihydroxybutoxycarbonyl.

Lower alkoxy-lower alkoxycarbonyl is, for example, 2-methoxyethoxycarbonyl, 1- or 2-ethoxyethoxycarbonyl, 2- or 3-methoxypropoxycarbonyl or 2-, 3- or 4-methoxybutoxycarbonyl.

Hydroxyalkyl is, for example, hydroxymethyl or hydroxyethyl, but also hydroxypropyl or hydroxybutyl.

N-lower alkylcarbamoyl is, for example, N-methylcarbamoyl, N-ethylcarbamoyl, N-propylcarbamoyl, N-isopropylcarbamoyl or N-butylcarbamoyl and N,N-di-lower alkylcarbamoyl is, for example, N,N-dimethylcarbamoyl, N,N-diethylcarbamoyl or N,N-methylethylcarbamoyl.

N-Hydroxy-lower alkylcarbamoyl is, for example, N-hydroxymethylcarbamoyl or N-2-hydroxyethylcarbamoyl and, N,N-dihydroxy-lower alkylcarbamoyl is, for example, N,N-2,3-dihydroxypropylcarbamoyl.

Salts of compounds of the formula I according to the invention are preferably pharmaceutically acceptable salts, such as corresponding acid addition salts and/or, when $R_2$ is 1-carboxy-lower alkyl, internal salts or salts with bases. Suitable acid addition salts are, for example, salts with inorganic acids, such as mineral acids, or organic acids, such as sulphamic acids, for example cyclohexylsulphamic acid, optionally unsaturated dicarboxylic acids, or carboxylic acids optionally additionally substituted by hydroxy or additionally containing oxo and/or carboxy, or sulphonic acids. Mineral acids are, for example, sulphuric acid or hydrohalic acids, such as hydrobromic or hydrochloric acid. There come into consideration as optionally unsaturated dicarboxylic acids, for example oxalic acid, malonic acid, fumaric acid or maleic acid, and there are used as carboxylic acids optionally additionally substituted by hydroxy or additionally containing oxo and/or carboxy, for example tartaric acid, malic acid, pyruvic acid or citric acid. Sulphonic acids are, for example, benzenesulphonic, p-toluenesulphonic or methanesulphonic acid.

Suitable salts with bases are, for example, metal, such as alkali metal or alkaline earth metal, salts, for example sodium, potassium or magnesium salts, transition metal salts, such as zinc or copper salts, or salts with ammonia or salts of substituted organic amines such as morpholine, thiomorpholine, piperidine and pyrrolidine, such as mono-, di- or tri-lower alkylamines or mono-, di- or tri-hydroxy-lower alkylamines, for example mono-, di- or tri-ethanolamine. Mono-lower alkylamines are, for example, ethylamine or tert.-butylamine. Di-lower alkylamines are, for example, diethylamine or dipropylamine, and there come into consideration as tri-lower alkylamines, for example, triethylamine, tributylamine or dimethylpropylamine.

The compounds of the formula I have valuable pharmacological properties. In particular they exhibit a pronounced antinociceptive (analgesic) activity, which may be demonstrated, for example, by the acetic acid-writhing syndrome in rats in a dosage range of from approximately 1 to approximately 30 mg/kg p.o. and by the phenyl-p-benzoquinone-writhing test in mice in a dosage range of from approximately 1 to approximately 30 mg/kg p.o..

In addition, they have a marked anti-inflammatory and anti-arthritic activity, which may be demonstrated by suppression of kaolin paw oedema in the normal rat in a dosage range of from approximately 10 to 100 mg/kg p.o., and which, in addition, may be demonstrated by the suppression of carrageenin paw oedema in the rat, analogously to the method described by Pasquale et al., Agents and Actions, 5, 256 (1976), in doses of approximately 3 to approximately 300 mg/kg p.o..

Furthermore, in curative administration with administration, four times, of approximately 10 to 100 mg/kg p.o., the compounds of the formula I suppress kaolin paw oedema of the adjuvant-arthritis rat.

The compounds of the formula I are therefore excellently suitable as medicaments for the treatment of inflammatory disorders, especially those in the rheumatic and arthritic field, as antiphlogistics and/or as peripheral analgesics.

The invention relates, for example, to compounds of the formula I in which $R_1$ represents phenyl optionally substituted by lower alkyl, by lower alkoxy, by optionally halogen-containing lower alkylthio, lower alkanesulphinyl or lower alkanesulphonyl, by sulphamoyl optionally mono- or di-substituted by lower alkyl, and/or by halogen, or represents 5- or 6-membered monocyclic heteroaryl optionally containing lower alkyl, lower alkoxy and/or halogen and having as hetero atom nitrogen, oxygen or sulphur, or nitrogen and, in addition, sulphur or oxygen, $R_2$ represents 1-carboxy-lower alkyl of the formula $-CH(R_3)-R_2'$, in which $R_2'$ represents carboxy, lower alkoxycarbonyl optionally substituted by lower alkyl-, lower alkoxy- or halogen-containing phenyl or pyridyl, by hydroxy or by lower alkoxy, or represents carbamoyl optionally substituted once by hydroxy or amino, once or twice by lower alkyl or hydroxy-lower alkyl, or twice by 4- to 7-membered lower alkylene or 3-oxa-, 3-thia- or 3-aza-alkylene, $R_3$ is hydrogen or lower alkyl, Ph is 1,2-phenylene optionally substituted by lower alkyl, lower alkoxy, halogen and/or trifluoromethyl, and alk is lower alkylene separating the methine group from the imino group by from 1 to 3 carbon atoms or lower alkylene separating the methine group from the imino group by 2 carbon atoms, and their salts, especially pharmaceutically acceptable salts.

Among the above there are included, for example, compounds of the formula I in which $R_1$ represents phenyl optionally substituted by lower alkyl, lower alkoxy, lower alkylthio, halo-lower alkylthio, lower alkanesulphinyl, halo-lower alkanesulphinyl, lower alkanesulphonyl, halo-lower alkanesulphonyl, sulphamoyl, N-mono- or N,N-di-lower alkylsulphamoyl and/or halogen, or represents pyrrolyl, furyl, thienyl, thiazolyl, pyridyl or pyrimidyl each optionally substituted by lower alkyl, lower alkoxy and/or halogen, $R_2$ represents a group of the formula $-CH(R_3)-R_2'$ in which $R_2'$ is carboxy, phenyl- or pyridyl-lower alkoxycarbonyl optionally substituted by lower alkyl, lower alkoxy or halogen, hydroxy- or lower alkoxy-lower alkoxycarbonyl, lower alkoxycarbonyl, carbamoyl, N-hydroxycarbamoyl, N-aminocarbamoyl, N-mono- or N,N-di-lower alkylcarbamoyl or -hydroxy-lower alkylcarbamoyl, or carbamoyl substituted by 4- to 7-membered lower alkylene, or 3-oxa-, 3-thia- or 3-aza-alkyleneaminocarbonyl, $R_3$ represents hydrogen or lower alkyl, Ph represents 1,2-phenylene optionally substituted by lower alkyl, lower alkoxy, halogen and/or trifluoromethyl and alk represents lower alkylene separating the methine group from the imino group by from 1 to 3 carbon atoms or lower alkenylene separating the methine group from the imino group by 2 carbon atoms, and their salts, especially pharmaceutically acceptable salts.

The invention relates especially to compounds of the formula I in which $R_1$ represents phenyl optionally substituted by lower alkyl having up to and including 4 carbon atoms, such as methyl, by lower alkoxy having up to and including 4 carbon atoms, such as methoxy, by halo-lower alkylthio having up to and including 4 carbon atoms, such as chloromethylthio, by lower alkylthio having up to and including 4 carbon atoms, such as methylthio, by halo-lower alkanesulphinyl having up to and including 4 carbon atoms, such as chloromethanesulphinyl, by lower alkanesulphinyl having up to and including 4 carbon atoms, such as methanesulphinyl, by halo-lower alkanesulphonyl, such as chloromethanesulphonyl, by lower alkanesulphonyl having up to and including 4 carbon atoms, such as methanesulphonyl, by sulphamoyl, by N-mono- or N,N-di-lower alkanesulphamoyl each having up to and including 4 carbon atoms in the alkyl radical, such as N-methanesulphamoyl or N,N-diethylsulphamoyl, and/or by halogen having an atomic number of up to and including 35, such as chlorine, or represents pyridyl, such as 2-, 3- or 4-pyridyl, or thienyl, such as 2-thienyl, each optionally substituted by lower alkyl having up to and including 4 carbon atoms, such as methyl, by lower alkoxy having up to and including 4 carbon atoms, such as methoxy, and/or by halogen having an atomic number of up to and including 35, such as chlorine, $R_2$ represents a group of the formula —CH($R_3$)—$R_2'$ in which $R_2'$ represents carboxy, phenyl- or pyridyl-lower alkoxycarbonyl, such as 2-, 3- or 4-pyridyl-lower alkoxycarbonyl, optionally substituted by lower alkyl having up to and including 4 carbon atoms, such as methyl, by lower alkoxy having up to and including 4 carbon atoms, such as methoxy, and/or by halogen, such as chlorine, lower alkoxycarbonyl, such as methoxycarbonyl, mono- or di-hydroxy-lower alkoxycarbonyl, such as 2-hydroxyethoxy- or 2,3-dihydroxypropoxycarbonyl, lower alkoxy-lower alkoxycarbonyl such as 2-methoxyethoxycarbonyl, N-hydroxy- or N-aminocarbamoyl, N-mono- or N,N-di-lower alkylcarbamoyl, such as N-methyl- or N,N-diethylcarbamoyl, or carbamoyl, $R_3$ is hydrogen or lower alkyl having up to and including 4 carbon atoms, such as methyl, Ph is 1,2-phenylene optionally substituted by lower alkyl having up to and including 4 carbon atoms, such as methyl, by lower alkoxy having up to and including 4 carbon atoms, such as methoxy, and/or by halogen having up to and including an atomic number of 35, such as fluorine and alk is 1,2-ethylene, and their salts, especially pharmaceutically acceptable salts.

The invention relates first and foremost to compounds of the formula I in which $R_1$ represents phenyl, optionally substituted by halogen, lower alkylthio, lower alkanesulphinyl, lower alkanesulphonyl, halo-lower alkylthio and/or sulphamoyl, or pyridyl or thienyl, $R_2$ represents a group of the formula —CH$_2$—$R_2'$ in which $R_2'$ represents carboxy, lower alkoxycarbonyl or carbamoyl, Ph represents 1,2-phenylene optionally substituted by lower alkoxy, lower alkyl and/or halogen, and alk is 1,2-ethylene or vinylene, and their salts, especially pharmaceutically acceptable salts.

The invention relates preferably to compounds of the formula I in which $R_1$ represents phenyl, optionally substituted by halogen having an atomic number of up to and including 35, such as chlorine, by lower alkylthio having up to and including 4 carbon atoms, such as methylthio, by lower alkanesulphinyl having up to and including 4 carbon atoms, such as methanesulphinyl, by halo-lower alkylthio having up to and including 4 carbon atoms, such as chloromethylthio and/or by sulphamoyl, pyridyl, especially 2-pyridyl, or thienyl, especially 2-thienyl, $R_2$ represents a group of the formula —CH$_2$—$R_2'$ in which $R_2'$ represents carboxy, lower alkoxycarbonyl having up to and including 5 carbon atoms, such as ethoxycarbonyl, or carbamoyl, Ph represents 1,2-phenylene optionally substituted by lower alkoxy having up to and including 4 carbon atoms, such as methoxy, by lower alkyl having up to and including 4 carbon atoms, such as methyl, and/or by halogen having an atomic number of up to and including 35, such as fluorine, and alk is 1,2-ethylene or vinylene, and their salts, especially pharmaceutically acceptable salts.

The invention relates in an especially preferred manner to compounds of the formula I in which $R_1$ represents phenyl optionally substituted in the p-position by halo-lower alkylthio having up to and including 4 carbon atoms, such as chloromethylthio, by lower alkylthio having up to and including 4 carbon atoms, such as methylthio, by lower alkanesulphinyl having up to and including 4 carbon atoms, such as methanesulphinyl, or by halogen having an atomic number of up to and including 35, such as chlorine, or in the 3-position by sulphamoyl and, in addition, in the 4-position by halogen having an atomic number of up to and including 35, such as chlorine, or pyridyl, especially 2-pyridyl, or thienyl, especially 2-thienyl, $R_2$ represents a group of the formula —CH$_2$—$R_2'$ in which $R_2'$ represents carboxy, lower alkoxycarbonyl having up to and including 5 carbon atoms, such as ethoxycarbonyl, or carbamoyl, Ph represents 1,2-phenylene optionally substituted in the 4-position in relation to the bonded nitrogen atom by lower alkoxy having up to and including 4 carbon atoms, such as methoxy, in the 3- and 5-position by lower alkyl having up to and including 4 carbon atoms, such as methyl, or in the 4-position by halogen having an atomic number of up to and including 35, such as fluorine, and alk is 1,2-ethylene or vinylene, and their salts, especially pharmaceutically acceptable salts.

The invention relates especially preferably to compounds of the formula I in which $R_1$ represents phenyl optionally substituted in the p-position by lower alkylthio having up to and including 4 carbon atoms, such as methylthio, by lower alkanesulphinyl having up to and including 4 carbon atoms, such as methanesulphinyl, or by halogen having an atomic number of up to and including 35, such as chlorine, $R_2$ represents lower alkoxycarbonylmethyl, such as ethoxycarbonylmethyl, Ph represents 1,2-phenylene optionally mono-substituted in the 4-position in relation to the bonded nitrogen atom by lower alkoxy having up to and including 4 carbon atoms, such as methoxy, or in the 4-position by halogen having an atomic number of up to and including 35, such as fluorine, and alk is 1,2-ethylene, and their salts, especially pharmaceutically acceptable salts.

The invention relates especially preferably to compounds of the formula I in which $R_1$ represents unsubstituted phenyl, p-methoxyphenyl or p-methanesulphinylphenyl, $R_2$ represents in each case ethoxycarbonylmethyl, Ph represents in each case 1,2-phenylene substituted in the 4-position, in relation to the nitrogen atom, by fluorine and alk represents in each case vinylene or in which $R_1$ represents unsubstituted 2-thienyl, unsubstituted phenyl, p-methylthiophenyl, p-methanesulphinylphenyl or p-methoxyphenyl, $R_2$ represents in each case carboxymethyl, Ph represents in each case 1,2-phenylene substituted in the 4-position, in relation to the nitrogen atom, by fluorine and alk represents in each case vinylene or in which R₁ represents in each case unsubstituted 2-thienyl, R₂ represents carboxymethyl or ethoxycarbonylmethyl, Ph represents in each case unsubstituted 1,2-phenylene and alk represents in each case vinylene or in which R₁ represents unsubstituted phenyl, R₂ represents carboxymethyl, Ph represents unsubstituted 1,2-phenylene and alk represents vinylene or in which R₁ represents 2-picolinyl or p-fluorophenyl, R₂ represents in each case carboxymethyl or ethoxycarbonylmethyl, Ph represents in each case 1,2-phenylene substituted in the 4-position, in relation to the nitrogen atom, by methoxy and alk represents in each case vinylene, and their salts, especially pharmaceutically acceptable salts.

The invention relates especially preferably to compounds of the formula I in which R₁ represents unsubstituted phenyl, p-methoxyphenyl or p-methanesulphinylphenyl, R₂ represents in each case ethoxycarbonylmethyl, Ph represents in each case 1,2-phenylene substituted in the 4-position, in relation to the nitrogen atom, by fluorine and alk represents in each case vinylene or in which R₁ represents unsubstituted phenyl, p-methylthiophenyl, p-methanesulphinylphenyl or p-methoxyphenyl, R₂ represents in each case carboxymethyl, Ph represents in each case 1,2-phenylene substituted in the 4-position, in relation to the nitrogen atom, by fluorine and alk represents in each case vinylene or in which R₁ represents in each case unsubstituted 2-thienyl, R₂ represents carboxymethyl or ethoxycarbonylmethyl, Ph represents in each case unsubstituted 1,2-phenylene and alk represents in each case vinylene or in which R₁ represents unsubstituted phenyl, R₂ represents carboxymethyl, Ph represents unsubstituted 1,2-phenylene and alk represents vinylene or in which R₁ represents 2-picolinyl or p-fluorophenyl, R₂ represents in each case carboxymethyl or ethoxycarbonylmethyl, Ph represents in each case 1,2-phenylene substituted in the 4-position, in relation to the nitrogen atom, by methoxy and alk represents in each case vinylene, and their salts, especially pharmaceutically acceptable salts.

The invention relates more especially to compounds of the formula I in which R₁ represents phenyl optionally substituted in the p-position by lower alkylthio having up to and including 4 carbon atoms, such as methylthio, by lower alkanesulphinyl having up to and including 4 carbon atoms, such as methanesulphinyl, or by halogen having up to and including an atomic number of 35, such as chlorine, R₂ represents carboxymethyl, Ph represents 1,2-phenylene optionally substituted in the p-position to the nitrogen atom by lower alkoxy having up to and including 4 carbon atoms, such as methoxy, or by halogen having up to and including an atomic number of 35, such as fluorine, and alk represents 1,2-ethylene, and their salts, especially their pharmaceutically acceptable salts.

The invention relates namely to the compounds of the formula I and their salts, especially their pharmaceutically acceptable salts, mentioned in the Examples.

The compounds of the formula I and their salts can be produced according to methods known per se, for example by splitting off H—Z₁ from compounds of the general formula

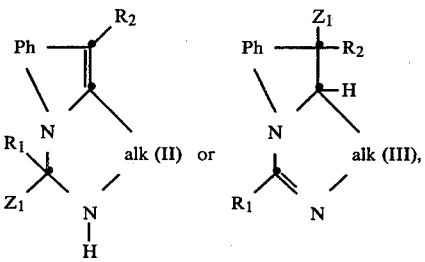

in which Z₁ represents optionally functionally modified hydroxy or mercapto, or from salts thereof, with the introduction of an additional bond, and, if desired, converting a compound obtainable according to the invention into a different compound of the formula I or converting a free compound obtainable according to the invention into a salt, or converting a salt obtainable according to the process into the free compound or into a different salt.

Functionally modified hydroxy or mercapto is, for example, hydroxy or mercapto etherified by a lower alkanol, such as methanol or ethanol, or by an optionally substituted aromatic alcohol, such as phenol, or hydroxy esterified by an inorganic acid, such as a mineral acid, for example a hydrohalic acid, such as hydrochloric acid, and represents, for example, lower alkoxy, such as methoxy, or optionally substituted aryloxy, such as phenoxy, lower alkylthio, such as methylthio, or halogen, such as chlorine or bromine.

H—Z₁ is split off in customary manner, for example spontaneously, by thermal means, i.e. by heating, and/or in the presence of a catalytic agent. The thermal splitting reaction is usually carried out in a temperature range of from approximately 50° to approximately 200° C. The catalytic agents used are, for example, basic or acidic catalysts, there being used as bases, for example alkali metal hydroxides, amides or hydrides, such as potassium hydroxide, sodium amide or sodium hydride, metal oxides, such as aluminium oxide, or especially organic nitrogen bases, such as tertiary amines, for example pyridine, quinoline or N,N-dimethylaniline, and as acidic catalysts, for example mineral acids or acidic salts or anhydrides thereof, such as sulphuric acid or phosphoric acids, hydrogen sulphates, such as alkali metal hydrogen sulphates, for example potassium hydrogen sulphate, phosphorus pentoxide, or mineral acid halides, such as sulphuric acid halides, for example sulphuryl chloride. The process is, if necessary, carried out in the presence of an inert solvent or diluent, in a closed vessel and/or under an inert gas, for example nitrogen.

Inert solvents and diluents are optionally substituted hydrocarbons, such as optionally halogenated aliphatic or aromatic hydrocarbons, for example chloroform or chlorobenzene, ethers, such as aliphatic, cycloaliphatic or aromatic ethers, for example diethyl ether, dioxan, tetrahydrofuran, diphenyl ether or anisole, ketones, such as aliphatic ketones, for example acetone or methylethylketone, amides, such as dialkylamides, for example dimethylformamide, or sulphoxides, such as di-lower alkylsulphoxides, for example dimethylsulphoxide.

Starting materials of the formulae II and III can be produced according to processes known per se, for example by cyclising compounds of the formula

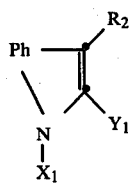
(IVa)

or salts thereof, in which $X_1$ represents hydrogen and $Y_1$ represents a group of the formula —alk—N-H—C(=$Z_1'$)($R_1$) or $X_1$ represents —C(=$Z_1'$)($R_1$) and $Y_1$ represents a group of the formula —alk—$NH_2$ and $Z_1'$ represents optionally functionally modified oxo, and, if desired, converting a so-obtainable free compound of the formula II into a different free compound, or into a salt, or converting a salt obtainable according to the process into the free compound or into a different salt.

Functionally modified oxo is, for example, thioxo, ketalised or thio-ketalised oxo, esterified dioxy, or imino. Ketalised oxo compounds are, for example, ketals with lower alkanols, such as methanol or ethanol, or lower alkanediols, such as ethylene glycol or propyleneglycols, for example 1,3-dihydroxypropane, and thio-ketals are, for example, thioketals with lower alkanethiols, for example methanethiol or ethanethiol, or lower alkanedithiols, such as 1,2-ethanedithiol, or propanedio-thiols, for example propane-1,3-dithiol.

Imino is, for example, imino optionally substituted by lower alkyl or phenyl, such as N-lower alkylimino, for example N-propylimino.

The cyclisation is carried out in known manner, for example in the presence of catalysts, such as acidic catalysts. These are, for example, mineral acids, such as sulphuric acid or polyphosphoric acid, mineral acid halides, such as sulphuryl chloride, or phosphorus halides, for example phosphorus pentachloride, or organic sulphonic acids, such as benzenesulphonic, p-toluenesulphonic or methanesulphonic acid. The cyclisation is, if necessary, carried out in one of the above-mentioned inert solvents or diluents, preferably while heating, for example in a temperature range of from approximately 20° to approximately 200° C., in a closed vessel and/or under inert gas, for example nitrogen.

In an advantageous embodiment of the aforedescribed process, compounds of the formula IVa are used as starting materials and cyclisation to compounds of the formula II and splitting off H-$Z_1$ from the compounds of the formula II are carried out in situ without isolation of the intermediates.

An especially advantageous embodiment of the aforedescribed process carried out by way of the compounds of the formula II consists, for example, in quaternising, especially with benzyl bromide, compounds of the formula

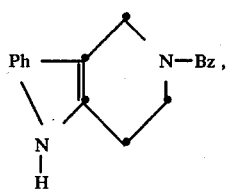
(IVd)

in which Bz represents an optionally substituted α-phenyl-lower alkyl radical, preferably benzyl, splitting the bond at the quaternary nitrogen atom by means of cyanides, such as alkali metal cyanides, for example sodium cyanide, and, in a resulting compound of the formula Ive

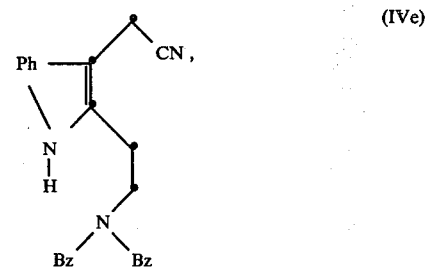
(IVe)

as desired solvolysing the cyano group, splitting off the benzyl groups by hydrogenolysis in the presence of a hydrogenation catalyst, for example palladium, and reacting the then free amino compound with a compound of the formula

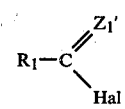

in which $Z_1'$ represents optionally functionally modified oxo and Hal represents halogen, and finally reacting by means of a cyclising agent, preferably a mineral acid halide, such as phosphorus oxychloride or phosphorus chloride, to form a compound of the formula II.

The compounds of the formula I or salts thereof may furthermore be produced by isomerising compounds of the formula

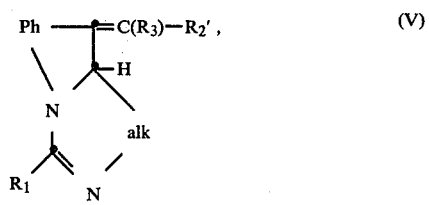
(V)

in which $R_2'$ represents optionally esterified or amidated carboxy, or salts thereof, and, if desired, converting a so-obtainable free compound of the formula I into a different free compound or into a salt, or converting a salt obtainable according to the process into the free compound or into a different salt.

The isomerisation of compounds of the formula V to compounds of the formula I is carried out in customary manner, if necessary by means of acids, such as mineral acids, for example sulphuric acid, bases, such as alkali metal hydroxides or carbonates, for example sodium hydroxide or potassium carbonate, or such as by means of organic amides, for example tertiary amines, such as pyridine, or by applying energy, such as at temperatures of from 100° C., optionally in the presence of a catalytic agent, such as a borate or phosphate, for example an alkali metal borate or phosphate and, if necessary, in a solvent or diluent, in a closed vessel and/or under inert gas, for example nitrogen.

Inert solvents and diluents are optionally substituted hydrocarbons, such as optionally halogenated aliphatic or aromatic hydrocarbons, for example chloroform or chlorobenzene, ethers, such as aliphatic, cycloaliphatic or aromatic ethers, for example diethyl ether, dioxan, diphenyl ether or anisole, ketones, such as aliphatic ketones, for example acetone or methylethylketone, amides, such as dialkylamides, for example dimethylformamide, or sulphoxides, such as dilower alkylsulphoxides, for example dimethylsulphoxide.

Starting materials of the formula V or salts thereof can be produced according to methods known per se, for example by reacting compounds of the formula

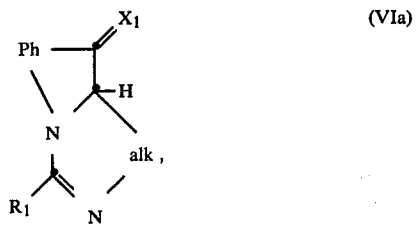

in which $X_1$ represents oxo or thioxo, with compounds of the formula $P(Z_2)_3{=}C(R_3){-}R_2'$ or $X_1{=}P(Z_3)_2{-}CH(R_3){-}R_2'$ respectively, which may be in the form of phosphonium ylides or in the form of phosphoranes, and in which $X_1$ represents oxo or thioxo, $Z_2$ represents alkyl and/or phenyl, $Z_3$ represents alkyl and/or phenyl, or alkoxy and/or phenoxy, and $R_3$ represents hydrogen or lower alkyl. Starting materials of the formula V or salts thereof may likewise be produced, for example by reacting compounds of the formula

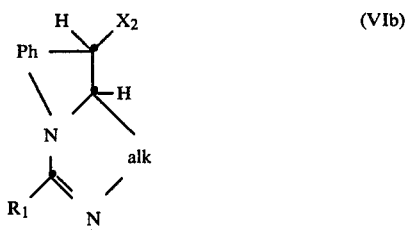

in which $X_2$ represents a group of the formula $-C(R_3){=}X_2'$ and $X_2'$ represents optionally functionally modified oxo, with hydrogen cyanide or a salt, for example an alkali metal salt, thereof. After solvolysis, which then optionally follows, a compound of the formula $Z_4$-$Z_5$ is split off from so-obtainable intermediates of the formula

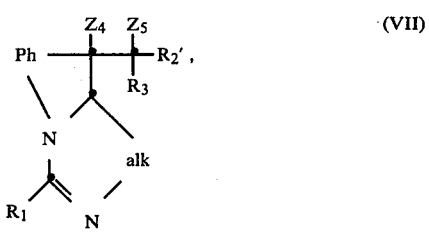

in which $Z_4$ represents hydroxy or thio optionally present in salt form and $Z_5$ represents a radical of the formula $-P^{\oplus}(Z_2)_3$ or $-P^{\oplus}(Z_3)_2-O^{\ominus}$, or $Z_4$ represents hydrogen and $Z_5$ represents hydroxy or mercapto.

Alkoxy is, for example, lower alkoxy, such as methoxy, ethoxy, propoxy or butoxy. Optionally functionally modified oxo is oxo, thioxo or imino optionally substituted by lower alkyl or phenyl.

In an advantageous embodiment of the above-described process for the manufacture of compounds of the formula I, for example using compounds of the formula VII as starting materials, the manufacture of compounds of the formula V and the isomerisation according to the invention can be carried out in situ.

The splitting off of $Z_4$-$Z_5$ is carried out in customary manner, for example by the application of energy, for example a reaction temperature of from approximately 50° to approximately 200° C., or in the presence of a catalytic agent. Such agents are, for example, basic or acidic catalysts, there being used as bases, for example alkali metal hydroxides, amides, carbonates or hydrides, such as potassium hydroxide, sodium amide, potassium carbonate or sodium hydride, metal oxides, such as aluminium oxide, or organic nitrogen bases, such as tertiary amines, for example pyridine, quinoline or N,N-dimethylaniline, and as acidic catalysts, for example mineral acids, such as sulphuric acid, hydrogen sulphates, such as alkali metal hydrogen sulphates, for example potassium hydrogen sulphate, polyphosphoric acid, mineral acid anhydrides, such as phosphorus pentoxide, or mineral acid halides, such as sulphuric acid halides, for example sulphuryl chloride.

The method for the formation of starting materials of the formula V is, if necessary, carried out in the presence of an inert solvent or diluent, in a closed vessel and/or under inert gas, for example nitrogen.

Compounds of the formulae VIa or VIb may, for their part, be produced according to analogous processes that are known per se, for example by condensing compounds of the formula

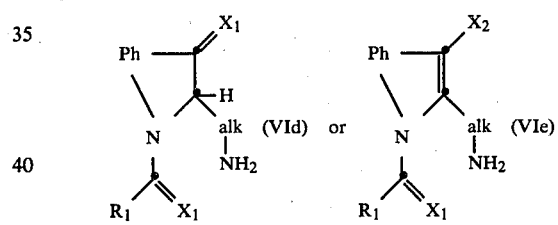

in the presence of a condensing agent. Suitable condensing agents are, for example, acids, such as mineral acids, for example sulphuric acid, polyphosphoric acid or a hydrohalic acid, for example hydrochloric acid, or phosphoric acid halides, such as phosphorus oxychloride or phosphorus trichloride.

Phosphoranes of the formula $P(Z_2)_3{=}C(R_3){-}R_2'$ and their phosphonium ylides can be produced according to methods known per se, for example by reacting phosphines of the formula $P(Z_2)_3$ with quaternary ammonium bases of the formula $R_2'-CH(R_3)-N^{\oplus}$ $(alk')_3 B^{\ominus}$ in which alk' represents an alkyl radical, such as a lower alkyl radical, and $B^{\ominus}$ represents an anion, such as a halide or hydroxyl anion, and by subsequent reaction with strong bases, such as alkali metal organyls, for example butyllithium or phenyllithium. The corresponding quaternary ammonium bases are obtained likewise by reaction of phosphines $P(Z_2)_3$ with known compounds of the formula $R_2$-Hal in the presence of bases, such as alkali metal hydroxides, lower alkanolates, hydrides or amides, for example sodium hydroxide, sodium methanolate, potassium hydride or potassium amide.

Compounds of the formula $X_1{=}P(Z_3)_2{-}CH(R_3){-}R_2'$ can be produced, for example, by reacting compounds of the formula P(Z₃)₃ in which Z₃ represents alkoxy or phenoxy, with compounds of the formula Hal—CH(R₃)—R₂' in which Hal represents halogen.

Compounds of the formula VId are obtainable by acylation of compounds of the formula

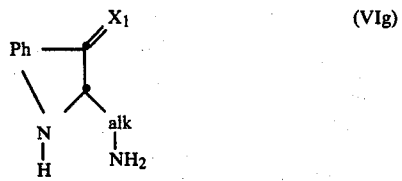

with compounds of the formula

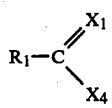

in which X₄ represents halogen or acyl.

The compounds of the formula I or salts thereof can furthermore be produced, for example by cyclising a compound of the general formula

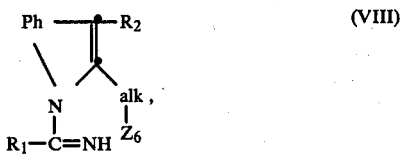

in which Z₆ represents optionally functionally modified hydroxy or mercapto, or amino, or a salt thereof, and, if desired, converting a so-obtainable free compound of the formula I into a different free compound or into a salt or converting a salt obtainable according to the process into the free compound or into a different salt.

Functionally modified hydroxy or mercapto is, for example, hydroxy or mercapto etherified by lower alkanol, such as methanol or ethanol, or by an optionally substituted aromatic alcohol, such as phenol, or hydroxy or mercapto esterified by a suitable anhydride, such as acetic anhydride, by an organic acid, such as sulphonic acid, for example lower alkylsulphonic or optionally substituted arylsulphonic acid, such as methanesulphonic or p-toluenesulphonic acid, or by an inorganic acid, such as a mineral acid, for example hydrohalic acid, such as hydrochloric acid, and represents, for example, lower alkoxy, such as methoxy, or optionally substituted aryloxy, such as phenoxy, lower alkylthio, such as methylthio, or lower alkanoyloxy, such as acetoxy, lower alkanesulphonyloxy or optionally substituted arylsulphonyloxy, such as methanesulphonyloxy or p-toluenesulphonyloxy, or halogen, such as chlorine or bromine.

The cyclisation is carried out in a manner known per se, for example in the presence of a condensing agent, such as an acidic condensing agent. Included among these are, for example, acids, such as mineral acids, for example sulphuric acid or polyphosphoric acid, and mineral acid halides, such as phosphoric acid halides, for example phosphorus oxychloride, phosphorus tribromide or phosphorus pentachloride. The reaction is, if necessary, carried out in a solvent or diluent, in a temperature range of from approximately 20° to approximately 200° C., in a closed vessel and/or under an inert gas, for example nitrogen.

Inert solvents and diluents are optionally substituted hydrocarbons, such as aliphatic or aromatic halogenated hydrocarbons, for example chloroform or chlorobenzene, optionally mixed ethers, such as aliphatic, cycloaliphatic or aromatic ethers, for example diethyl ether, dioxan, diphenyl ether or anisole, ketones, such as aliphatic ketones, such as acetone or methylethylketone, amides, such as dialkylamides, for example dimethylformamide, or sulphoxides, such as lower alkylsulphoxides, for example dimethylsulphoxide.

The starting materials of the formula VIII can be produced according to methods known per se, for example by substituting the primary amino group in compounds of the formula

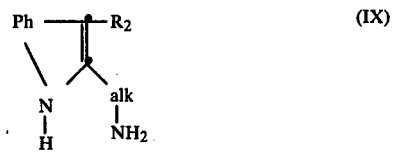

by means of alkali metal nitrites in the presence of acids, by hydroxy, optionally reactively esterifying this group, acylating the indole nitrogen with a compound of the formula R₁—COOH or with a functionally modified derivative thereof, and then forming the corresponding amidine with ammonia.

The acylation of the indole nitrogen is carried out according to a method known per se, for example by reaction with optionally functionally modified carboxy derivatives, such as acids, acid anhydrides or activated esters. Anhydridised carboxy in this process is anhydridised, for example, by inorganic acids, such as a hydrohalic acid, by hydrazoic acid, by hydrocyanic acid or by organic acids, such as lower alkanoic acids optionally substituted by halogen, for example acetic acid. Included among these are, for example, acid halides, for example acid chlorides, corresponding acid azides, acid nitriles or acyloxycarbonyl.

The acylation with a compound of the formula R₁—COOH or an optionally functionally modified derivative thereof is carried out in customary manner. When using an anhydride, especially an acid halide, as starting material, the acylation is preferably carried out in the presence of a strong base, for example an alkali metal hydride, for example sodium hydride, an alkali metal amide, for example sodium amide, or an alkali metal alcoholate, for example potassium methanolate.

The acylation, like the subsequent reaction with ammonia, is carried out, for example, in an inert solvent, such as an alkylated amide, for example N,N-dimethylformamide, an optionally halogenated hydrocarbon, for example chloroform or chlorobenzene, or a nitrile, for example acetonitrile, or in a mixture thereof, if necessary at reduced or elevated temperature and/or in an inert gas atmosphere.

The compounds of the formula IX may, for their part, be produced according to processes known per se, for example analogously to Fischer's indole synthesis by treating phenyl hydrazones or corresponding 1,3-substituted 4-piperidones with acids, such as with ethanolic hydrochloric acid, or by acylation and condensation of correspondingly substituted α-hydroxyketones with optionally substituted anilines.

The compounds of the formula IX may furthermore, in a preferred embodiment, be produced, for example, by quaternising starting compounds of the formula

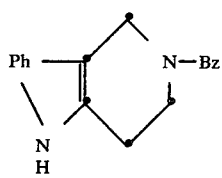 (IVd)

in which Bz represents an optionally substituted α-phenyl-lower alkyl radical, preferably benzyl, especially with benzyl bromide, and splitting the bond at the resulting quaternary nitrogen by means of a nucleophile, preferably by cyanides, and in a compound of the formula

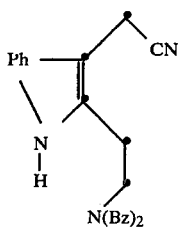 (IVe)

obtainable as intermediate, as desired solvolysing the cyano group and splitting off the benzyl groups, for example by hydrogenolysis in the presence of a hydrogenation catalyst, for example palladium.

The compounds of the general formula I or salts thereof can furthermore be produced, for example, from a compound of the formula

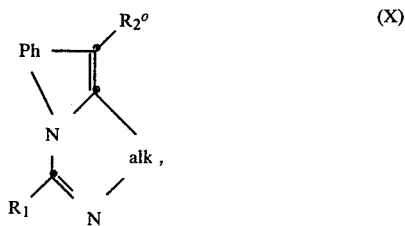 (X)

in which $R_2^o$ represents a group of the formula —CH($R_3$)—$R_2''$ and in which $R_3$ represents hydrogen or lower alkyl and $R_2''$ represents functionally modified carboxy different from $R_2'$, or a group of the formula —C(=O)—$N_2^{\oplus}B^{\ominus}$, in which $B^{\ominus}$ is the anion of a mineral acid, for example chloride, bromide or tetrafluoroborate, or represents methyl optionally oxidised to the stage of formyl, or salts thereof, by converting $R_2^o$ by solvolysis or oxidation into the group $R_2$ and, if desired, converting a so-obtainable free compound of the formula I into a different free compound or into a salt, or converting a salt obtainable in accordance with the process into the free compound or into a different salt. Functionally modified carboxy compounds and functionally modified carboxy compounds different from $R_2'$ are, for example optionally functionally modified ortho-ester groups, such as trihalo-, halo-di-lower alkoxy- or tri-lower alkoxymethyl groups, anhydridised carboxy, such as cyano, a group of the formula =C=O, cyano-, azido- or halocarbonyl, acyloxycarbonyl, such as acetoxycarbonyl, or derivatives of carboxy of the formula $R_2'$ or $R_2''$, in which oxo is optionally replaced by thio or optionally substituted imino, such as optionally esterified thiocarboxy, such as lower alkylthiocarboxy, for example ethylthiocarboxy, amidated thiocarboxyl, imino-esters, such as imide- or amide-halide groupings, for example iminochloromethyl or aminodichloromethyl, imino ether groupings, such as lower alkylimino ether or lower alkyleneimino ether groupings, for example methoxyiminomethylene or ethoxyiminomethylene, or amidino groups, such as amidino or lower alkylamidino, for example methylamidino.

Methyl oxidised to the formyl stage, or functionally modified groups thereof are, for example, optionally reactively esterified or etherified hydroxymethyl or optionally functionally modified formyl, such as hydroxymethyl, mono- or di-halomethyl, lower alkoxymethyl, formyl or formimino.

Functionally modified carboxy compounds, such as optionally functionally modified ortho-esters, anhydridised carboxy or acyloxycarbonyl can be solvolysed directly, or in several solvolysis steps, to free, esterified or amidated carboxy.

The solvolysis of $R_2''$ is carried out in known manner, for example by hydrolysis with water, by ammonolysis with ammonia, by aminolysis with a desired primary or secondary amine or by alcoholysis with a corresponding alcohol. The process is carried out, if necessary, in the presence of a catalyst, in a solvent or diluent in a closed vessel, in a temperature range of from approximately 0° to approximately 150° C. and/or under inert gas, for example nitrogen.

Catalysts are, for example, basic condensing agents, such as alkali metal or alkaline earth metal hydroxides, for example sodium, potassium or calcium hydroxide, or tertiary organic amines, such as pyridine, or trialkylamines, for example triethylamine, or acidic hydrolysing agents, such as mineral acids, for example hydrohalic acids, such as hydrochloric acid, or organic carboxylic or sulphonic acids, such as lower alkanecarboxylic acids or optionally substituted benzenesulphonic acids, for example acetic acid or p-toluenesulphonic acid.

Methyl optionally oxidised to the formyl stage, such as methyl, hydroxymethyl or formyl, or functionally modified derivatives thereof, such as halomethyl, for example chloromethyl, mercaptomethyl, thioformyl or optionally substituted formimino, may be oxidised directly or by way of several oxidation steps, optionally by way of hydroxymethyl or formyl, to carboxy. Etherified hydroxymethyl, preferably lower alkoxymethyl, for example ethoxymethyl, is oxidised, in the presence of an oxidising agent, to form esterified carboxy, especially lower alkoxycarbonyl. The reaction of formyl to form carbamoyl is carried out, for example by means of an amino compound in the presence of an oxidising agent, such as a transition metal oxide, for example manganese dioxide, and, if necessary, in the presence of a nucleophile, especially a cyanide.

Oxidation of $R_2''$ is carried out in customary manner, for example using customary oxidising agents. These are, for example, optionally catalytically activated oxygen, alkali metal salts of chromates or manganates, such as sodium chromate or potassium permanganate, or transition metal oxides, such as manganese dioxide or chromium trioxide. The oxidation is carried out, if necessary, in an inert solvent, in a closed vessel and/or while cooling or heating, for example at approximately 0° to approximately 150° C.

The starting materials of the formula X can be produced according to analogous processes, for example by reacting compounds of the formula

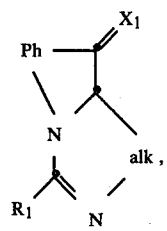
(VIa)

in which $X_1$ represents oxo or thioxo, with compounds of the formula $P(Z_2)_3$—$R_2^0$, which may be in the form either of phosphonium ylides or of phosphoranes, or $X_1$=$P(Z_3)_2$—$R_2^0$, and in which $Z_2$ represents alkyl and/or phenyl and $Z_3$ represents alkyl and/or phenyl, or represents alkoxy, such as lower alkoxy, and/or phenoxy, and $R_2''$ represents functionally modified carboxy different from $R_2'$, or a group of the formula —C(=O)N$_2^\oplus$B$^\ominus$ or methyl optionally oxidised to the formyl stage, splitting off from intermediates of the formula

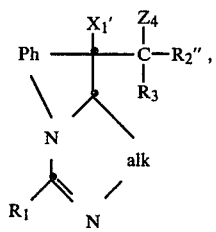
(VIh)

optionally obtainable in this manner, in which $X_1'$ represents —O$^\ominus$ or —S$^\ominus$ and $Z_4$ represents a radical of the formula —P$^\oplus(Z_2)_3$ or —P$^\oplus(X_1')(Z_3)_2$, respectively, a compound of the formula $X_1$=$P(Z_2)_3$ or $X_1$=$P(X_1')(Z_3)_2$ respectively, and isomerising a compound obtained in this manner to a compound of the formula X.

The reaction is usually carried out in an inert solvent, for example an optionally halogenated hydrocarbon, such as an aromatic compound, for example benzene or toluene, an ether, such as tetrahydrofuran or dioxan, or an amide, for example dimethylformamide, in a temperature range of from approximately 20° to approximately 150° C. and/or optionally in the presence of a catalyst, such as a base, for example an alkali metal alcoholate, such as potassium tert.-butanolate.

In a preferred embodiment, the starting materials of the formula X in which $R_2^0$ is a radical that can be converted by solvolysis or oxidation into $R_2$ are obtained, and starting, for example, from compounds of the formula

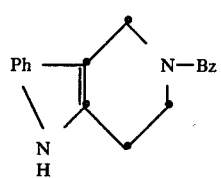
(IVd)

in which Bz represents an optionally substituted α-phenyl-lower alkyl radical, preferably benzyl, the tertiary nitrogen atom is quaternised, especially with benzyl chloride, the bond at the quaternary nitrogen atom is split by means of a strong base, such as by a cyanide, for example sodium cyanide, and in a resulting compound of the formula

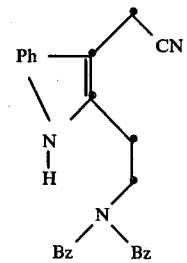
(IVe)

the cyano group is converted into $R_2^0$, for example by solvolysis to carboxy or lower alkoxycarbonyl and then reduction to hydroxymethyl or lower alkoxymethyl respectively, and the Bz groups are split off by hydrogenolysis in the presence of a hydrogenation catalyst. The compound obtained in this manner is then reacted with a compound of the formula

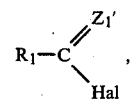

in which $Z_1'$ represents optionally functionally modified oxo and Hal represents halogen, and cyclisation to corresponding compounds of the formula X is carried out in the presence of a customary cyclising agent, such as a mineral acid halide, for example phosphorus oxychloride.

The compounds of the formula I in which $R_2$ represents amidated 1-carboxymethyl can further be produced by adding water and splitting off a proton in compounds of the formula

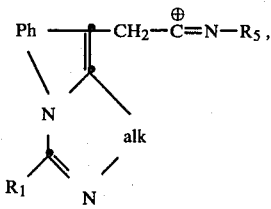
(XIa)

which are produced in situ by rearrangement of compounds of the formula

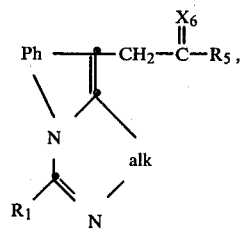
(XIb)

in which $R_5$ represents optionally substituted lower alkyl or phenyl and $X_6$ represents a radical of the formula $=N-OH$ or

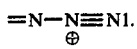

The reaction is carried out in customary manner, for example in the presence of an acidic catalyst, such as a mineral acid, for example sulphuric or phosphoric acid, and optionally while heating.

The starting materials of the formula XIb can be produced according to analogous processes, for example by reacting compounds of the formula

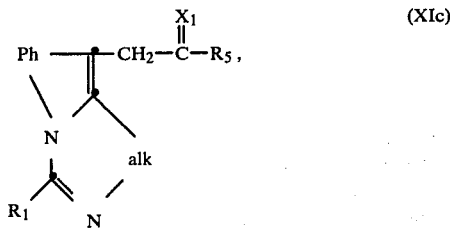

in which $X_1$ represents oxo or thioxo, with hydroxylamine or an acid addition salt thereof, or with an azide, such as an alkali metal azide, for example sodium azide.

Compounds of the formula I in which $R_2$ represents esterified or amidated 1-carboxy-lower alkyl and alk represents vinylene are produced, for example by dehydrogenating appropriate compounds of the formula

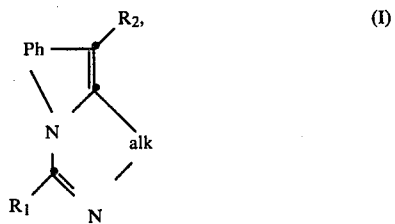

in which alk represents ethylene, with the splitting off of hydrogen with simultaneous formation of an additional bond, and, if desired, converting a compound obtainable according to the invention into a different compound of the formula I or converting a free compound of the formula I obtainable according to the invention into a salt obtainable according to the process into the free compound of the formula I or into a different salt.

The dehydrogenation is carried out in a manner known per se, especially at elevated temperature, for example in a temperature range of from room temperature, especially from approximately 100° to approximately 300° C., and with the use of dehydrogenating agent. Such agents are, for example, dehydrogenation catalysts, for example sub-group elements, preferably of the sub-group VIII, such as palladium or platinum, or salts thereof, such as ruthenium-triphenyl-phosphide-chloride, the catalysts optionally being supported on a suitable carrier, such as carbon, aluminium oxide or silicon dioxide. Other dehydrogenating agents are, for example, quinones, such as p-benzoquinone, for example tetrachloro-p-benzoquinone or 2,3-dichloro-5,6-dicyano-benzoquinone, or anthraquinones, for example phenanthrene-9,10-quinone. The reaction is carried out in an inert, optionally high-boiling, solvent, such as an ether, for example diphenyl ether, if necessary under pressure, in a closed vessel and/or under an inert gas, for example nitrogen.

Preferred dehydrogenation catalysts are suitable selenium derivatives, especially selenium dioxide or diphenylselenium-bis-(trifluoroacetate), furthermore diphenyl selenoxide. In an advantageous embodiment of the above-described process the dehydrogenation is carried out at elevated temperature when selenium dioxide is used. Using diphenylselenium-bis-(trifluoroacetate) the dehydrogenation is preferably carried out at room temperature.

The compounds of the formula I to be used as starting materials can be produced according to the aforedescribed processes.

A compound of the formula I obtainable according to the invention can be converted into a different compound of the formula I in a manner known per se.

If the group $R_2$ contains free carboxy, this can be converted according to esterification methods known per se into correspondingly esterified carboxy, for example by reacting optionally reactive modified carboxy or a salt thereof by alcoholysis with a desired alcohol, for example a reactive derivative thereof or an olefin derived therefrom, or by alkylation with diazo-lower alkane.

Suitable reactive functional carboxy derivatives are, for example, anhydrides, there being used as anhydrides especially mixed anhydrides, for example those with inorganic acids, such as hydrohalic acids, for example hydrochloric acid, or hydrazoic or hydrocyanic acids, or with organic carboxylic acids, such as lower alkanoic acids, for example acetic acid.

Reactive derivatives of an alcohol are, for example, carboxylic, phosphorous, sulphurous or carbonic acid esters, for example lower alkanecarboxylic acid esters, tri-lower alkylphosphite, di-lower alkylsulphite or pyrocarbonate, or mineral or sulphonic acid esters, for example chloride, bromide or sulphuric acid esters, benzenesulphonic, toluenesulphonic or methanesulphonic acid esters, of the alcohol concerned.

The esterification of free carboxy is carried out in the presence of a condensing agent. There come into consideration as agents that split off water by catalysis in the esterification with alcohols, for example acids, for example protonic acids, such as hydrochloric, hydrobromic, sulphuric, phosphoric, boric, benzenesulphonic and/or toluenesulphonic acid or Lewis acids, such as boron trifluoride etherate. Customary water-binding condensing agents are, for example, carbodiimides substituted by hydrocarbon radicals, for example N,N'-diethylcarbodiimide, N,N-dicyclohexylcarbodiimide or N-ethyl-N'-(3-dimethylaminopropyl)-carbodiimide.

Condensing agents for the esterification with reactive esters are, for example, basic condensing agents, such as inorganic bases, for example alkali metal or alkaline earth metal hydroxides or carbonates, such as sodium, potassium or calcium hydroxide or carbonate, or organic nitrogen bases, for example tertiary organic amines, such as triethylamine or pyridine. The esterification is advantageously carried out with the alcohol in excess. It is preferably carried out in an anhydrous medium, if necessary in the presence of an inert solvent, such as in halogenated hydrocarbons, for example chloroform or chlorobenzene, or in ethers, for example tetrahydrofuran or dioxan.

The reaction with an olefin can be carried out, for example, in the presence of an acidic catalyst, for example a Lewis acid, for example boron trifluoride, a sulphonic acid, for example p-toluenesulphonic acid, or especially a basic catalyst, for example sodium or potassium hydroxide, advantageously in an inert solvent, such as an ether, for example diethyl ether or tetrahydrofuran.

Furthermore, free carboxy or reactive functional carboxy derivatives can be converted into a desired amidated form by solvolysis with ammonia or a primary or secondary amine, it being possible also for hydroxylamines or hydrazines to be used, the solvolysis being carried out in customary manner with dehydration, optionally in the presence of a condensing agent. There are used as condensing agents preferably bases, for example inorganic bases, such as alkali metal hydroxides, for example sodium or potassium hydroxide, organic nitrogen bases, such as tert.-amines, for example pyridine, tributylamine or N-dimethylaniline, or tetrahalosilanes, such as tetrachlorosilane.

Further, compounds of the formula I obtainable according to the invention in which $R_2$ contains esterified carboxy as substituent, can be transesterified in customary manner, for example by reaction with a corresponding alcohol or a metal salt thereof, such as an alkali metal salt, for example the sodium or potassium salt, if necessary in the presence of a catalyst, for example a strong base, such as an alkali metal hydroxide, amide or alcoholates, for example potassium hydroxide, sodium amide or sodium methanolate, or a strong acid, such as a mineral acid, for example sulphuric acid, phosphoric acid or hydrochloric acid, or such as an organic sulphonic acid, for example an aromatic sulphonic acid, such as p-toluenesulphonic acid.

Esterified carboxy can furthermore be converted into the free carboxy group according to known processes, for example by hydrolysis in the presence of a catalyst. There come into consideration as catalysts preferably bases, for example alkali metal hydroxides, such as sodium or potassium hydroxide. Esterified carboxy may furthermore be converted into carboxy in customary manner, for example by solvolysis, optionally in the presence of a catalyst, for example an acidic or basic agent, or into amidated carboxy by ammonolysis or aminolysis with ammonia or with a primary or secondary amine. There are used as bases, for example alkali metal hydroxides, such as sodium or potassium hydroxides, and as acids, for example mineral acids, such as sulphuric acid, phosphoric acid or hydrochloric acid. Likewise, compounds of the formula I obtainable according to the invention in which the group $R_2$ contains an amidated carboxy substituent can be transformed according to methods known per se that split the amide bond and thus convert the carbamoyl into free carboxy. This operation is carried out in the presence of a catalyst, for example a base, such as an alkali metal or alkaline earth metal hydroxide or carbonate, for example sodium, potassium or calcium hydroxide or carbonate, or an acid, such as a mineral acid, for example hydrochloric acid, sulphuric acid or phosphoric acid.

If the group $R_2$ of the formula I contains an esterified carboxy group, this can be converted into an amidated carboxy group, for example by customary solvolysis, advantageously by an axcess of ammonia, or an amine containing at least one hydrogen atom, optionally in the presence of a catalyst. There are used as catalysts, for example acids, such as mineral acids, for example hydrochloric, sulphuric or phosphoric acid, or bases, such as alkali metal hydroxides, for example sodium or potassium hydroxide.

If the group $R_2$ of the formula I contains as substituent amidated carboxy, this can be converted into esterified carboxy, for example by customary solvolysis with an alcohol in the presence of a catalyst. The catalysts used are, for example, acidic catalysts, such as mineral acids, for example phosphoric acid, hydrochloric acid or sulphuric acid.

If the substituent $R_1$ of the formula I is substituted by lower alkylthio, this can be oxidised in customary manner to corresponding lower alkanesulphinyl or lower alkanesulphonyl. There come into consideration as suitable oxidising agents for the oxidation to the sulphoxide stage, for example, inorganic peracids, such as peracids of mineral acids, for example periodic acid or persulphuric acid, organic peracids, such as suitable percarboxylic or persulphonic acids, for example performic, peracetic, trifluoroperacetic, perbenzoic or p-toluenepersulphonic acid, or mixtures of hydrogen peroxide and acids, for example a mixture of hydrogen peroxide with acetic acid.

Frequently, the oxidation is carried out in the presence of suitable catalysts, and there should be mentioned as catalysts suitable acids, such as optionally substituted carboxylic acids, for example acetic or trifluoroacetic acid, or transition metal oxides, such as oxides of elements of sub-group VII, for example vanadium, molybdenum or tungsten oxide. The oxidation is carried out under mild conditions, for example at temperatures of approximately $-50°$ to approximately $+100°$ C.

The oxidation to the sulphone stage can also be carried out in corresponding manner, with dinitrogen tetroxide as catalyst in the presence of oxygen at low temperatures, as can also the direct oxidation of the lower alkylthio to lower alkanesulphonyl, except that usually the oxidising agent is used in excess.

Compounds of the formula I in which $R_1$ represents an aromatic radical substituted by lower alkylsulphinyl or lower alkylsulphonyl can be reduced according to methods known per se to the corresponding lower alkylthio compounds, and, starting from lower alkanesulphonyl derivatives, also to lower alkanesulphinyl. A suitable reducing agent is, for example, catalytically activated hydrogen, there being used noble metals or oxides, such as palladium, platinum or rhodium or their oxides, optionally supported on a suitable carrier, such as active carbon or barium sulphate. There also come into consideration reducing metal cations, such as tin-(II) lead(II), copper(I), manganese(II), titanium(II), vanadium(II), molybdenum(III) or tungsten(III) compounds, hydrogen halides, such as hydrogen chloride, hydrogen bromide or hydrogen iodide, hydrides, such as complex metal hydrides, for example lithiumaluminium hydride, sodium borohydride and tributyltin hydride, phosphorus compounds, such as phosphorus halides, for example phosphorus trichloride, phosphorus tribromide, phosphorus pentachloride or phosphorus oxychloride, phosphines, such as triphenylphosphine, or phosphorus pentasulphidepyridine, or sulphur compounds, such as mercaptans, thio acids, such as thiophosphoric acids or dithiocarboxylic acids, dithionite or sulphur/oxygen complexes, such as an iodine/pyridine/sulphur dioxide complex.

Resulting salts can be converted into free compounds in a manner known per se, for example by treating with an acidic reagent, such as a mineral acid, or a base, for example an alkali hydroxide solution.

Depending on the choice of starting materials and methods, the new compounds may be in the form of one of the possible isomers or mixtures thereof, for example, depending on the number of asymmetrical carbon atoms, as pure optical isomers, such as antipodes, or as mixtures of isomers, such as racemates, mixtures of diastereoisomers or mixtures of racemates.

Resulting mixtures of diastereoisomers and mixtures of racemates can be separated on the basis of the physicochemical differences of the consitituents, in known manner, into the pure isomers, diastereoisomers or racemates, for example by chromatography and/or fractional crystallisation.

Resulting racemates can furthermore be resolved into the optical antipodes by known methods, for example by recrystallisation from an optically active solvent, by means of microorganisms or by reacting an acidic end product with an optically active base that forms salts with the racemic acid, and separating the salts obtained in this manner, for example on the basis of their different solubilities, into the diastereoisomers, from which the antipodes can be liberated by the action of suitable agents. Advantageously, the more active of the two antipodes is isolated.

The compounds, including their salts, can also be obtained in the form of their hydrates, or include other solvents used for the crystallisation.

Owing to the close relationship between the new compounds in free form and in the form of their salts, there are herein to be understood by the free compounds or their salts accordingly and appropriately optionally also the corresponding salts or free compounds respectively.

The invention relates also to those embodiments of the process according to which compounds obtainable as intermediates at any stage of the process are used as starting materials and the remaining steps are carried out, or a starting material is used in the form of a salt or especially is formed under the reaction conditions.

In the process of the present invention, there are preferably used as starting materials those that result in compounds described at the beginning as being especially valuable. The invention relates also to novel starting materials and processes for their manufacture.

The pharmaceutical preparations according to the invention, which contain compounds of the formula I or pharmaceutically acceptable salts thereof, are those for enteral, such as oral or rectal, and parenteral, administration as well as for topical administration to warm-blooded animals, that contain the pharmacological active substance alone or together with a pharmaceutically acceptable carrier. The dosage of the active substance depends on the species of warm-blooded animal, the age and the individual condition, and on the method of administration. Normally, where administration is oral and the warm-blooded animal weighs approximately 75 kg, an approximate daily dosage of 30 to 300 mg, advantageously divided into several equal portions, is estimated.

The new pharmaceutical preparations contain, for example, from approximately 10% to approximately 80%, preferably from approximately 20% to approximately 60%, of the active substance. Pharmaceutical preparations according to the invention for enteral or parenteral administration are, for example, those in dosage unit forms, such as dragées, tablets, capsules or suppositories, or also ampoules. These are produced in a manner known per se, for example by means of conventional mixing, granulating, coating, dissolving or lyophilising processes. Thus, pharmaceutical preparations for oral administration can be obtained by combining the active substance with solid carriers, optionally granulating a resulting mixture, and processing the mixture or granulate to form tablets or dragée cores, if desired or necessary after the addition of suitable adjuncts.

Suitable carriers are especially fillers, such as sugar, for example lactose, saccharose, mannitol or sorbitol, cellulose preparations and/or calcium phosphates, for example tricalcium phosphate or calcium hydrogen phosphate, also binders, such as starch pastes using, for example, corn, wheat, rice or potato starch, gelatin, tragacanth, methylcellulose and/or polyvinylpyrrolidone, and/or, if desired, disintegrators, such as the above-mentioned starches, and also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium or calcium stearate, and/or polyethyleneglycol. Dragée cores are provided with suitable, optionally gastric juice-resistant, coatings, there being used, inter alia, concentrated sugar solutions, which optionally contain gum arabic, talc, polyvinylpyrrolidone, polyethyleneglycol and/or titanium dioxide, lacquer solutions in suitable organic solvents or solvent mixtures, or, to produce gastric juice-resistant coatings, solutions of suitable cellulose preparations, such as acetylcellulosephthalate or hydroxypropylmethylcellulosephthalate. Colouring matter or pigments may be added to the tablets or dragée coatings, for example for identification purposes or for indicating different doses of active substance.

Other pharmaceutical preparations for oral administration are dry-filled capsules made of gelatin, and soft sealed capsules consisting of gelatin and a plasticiser, such as glycerin or sorbitol. The dry-filled capsules may contain the active substance in the form of a granulate, for example in admixture with fillers, such as lactose, binders, such as starches, and/or glidants, such as talc or magnesium stearate, and optionally stabilisers. In soft capsules the active substance is preferably dissolved or suspended in suitable liquids, such as fatty oils, paraffin oil or liquid polyethyleneglycols, it likewise being possible for stabilisers to be added.

There come into consideration as rectally administrable pharmaceutical preparations, for example suppositories consisting of a combination of the active substance with a suppository base. Suitable suppository bases are, for example, natural or synthetic triglycerides, paraffin hydrocarbons, polyethyleneglycols or higher alkanols. It is also possible to use gelatin rectal capsules that contain a combination of the active substance with a base, there coming into consideration as base substances, for example liquid triglycerides, polyethyleneglycols or paraffin hydrocarbons.

Especially suitable forms for parenteral administration are aqueous solutions of an active substance in water-soluble form, for example a water-soluble salt, or suspensions of the active substance, such as corresponding oily injection suspensions, suitable lipophilic solvents or vehicles, such as fatty oils, for example sesame oil, or synthetic fatty acid esters, for example ethyloleate or triglycerides, being used, or aqueous injection suspensions that contain viscosity-increasing substances, for example sodium carboxymethylcellulose, sorbitol and/or dextran and optionally also stabilisers.

For topical administration, there come into consideration especially creams, ointments, pastes, foams, tinctures and solutions that contain from approximately 0.5 to approximately 20% of the active substance.

Creams are oil-in-water emulsions that consist of more than 50% of water. As oily base there are used especially fatty alcohols, for example lauryl, cetyl or stearyl alcohol, fatty acids, for example palmitic or stearic acid, liquid-to-solid waxes, for example isopropylmyristate, wool wax or beeswax, and/or hydrocarbons, for example Vaseline (petrolatum) or paraffin oil. There come into consideration as emulsifiers surface-active substances with predominantly hydrophilic properties, such as corresponding non-ionic emulsifiers, for example fatty acid esters of polyalcohols or ethylene oxide adducts thereof, such as polyglycerin fatty acid esters or polyoxyethylene-sorbitan-fatty acid esters (Tweens), also polyoxyethylene fatty alcohol ethers or fatty acid esters, or corresponding ionic emulsifiers, such as alkali metal salts of fatty alcohol sulphates, for example sodium lauryl sulphate, sodium cetyl sulphate or sodium stearyl sulphate, which are usually used in the presence of fatty alcohols, for example cetyl alcohol or stearyl alcohol. Additives to the aqueous phase are, inter alia, agents that reduce the drying-out of creams, for example polyalcohols, such as glycerin, sorbitol, propyleneglycol and/or polyethyleneglycol, and also preservatives, odoriferous substances, etc.

Ointments are water-in-oil emulsions that contain up to 70%, but preferably from approximately 20% to approximately 50%, water or aqueous phases. There come into consideration as fatty phase especially hydrocarbons, for example Vaseline, paraffin oil and/or hard paraffins, which, to improve the water-binding capacity, preferably contain suitable hydroxy compounds, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the aqueous phase are, inter alia, moisture-retaining agents, such as polyalcohols, for example glycerin, propyleneglycol, sorbitol and/or polyethyleneglycol, and preservatives, odoriferous substances etc.

Fatty ointments are anhydrous and contain as base especially hydrocarbons, for example paraffin, Vaseline and/or liquid paraffins, also natural or partially synthetic fat, for example coconut fatty acid triglyceride, or preferably hardened oils, for example hydrogenated peanut oil or castor oil, also fatty acid partial esters of glycerin, for example glycerin mono- and di-stearates, as well as, for example, the fatty alcohols that increase the ability to absorb water, the emulsifiers and/or the additives, mentioned in connection with the ointments.

Pastes are creams and ointments with secretion-absorbing powder constituents, such as metal oxides, for example titanium oxide or zinc oxide, and also talc and/or aluminium silicates which serve to bind any moisture or secretions present.

Foams are dispensed from pressure containers and are liquid oil-in-water emulsions in aerosol form, halogenated hydrocarbons, such as chlorofluoro-lower alkanes, for example dichlorodifluoromethane and dichlorotetrafluoroethane, being used as propellants. As oil phase there are used, inter alia, hydrocarbons, for example paraffin oil, fatty alcohols, for example cetyl alcohol, fatty acid esters, for example isopropylmyristate, and/or other waxes. As emulsifiers there are used, inter alia, mixtures of emulsifiers with predominantly hydrophilic properties, such as polyoxyethylene-sorbitan-fatty acid esters (Tweens), and emulsifiers with predominantly lipophilic properties, such as sorbitan fatty acid esters (Spans). In addition there are the customary additives, such as preservatives etc.

Tinctures and solutions usually have an aqueous ethanolic base, to which there are added, inter alia, polyalcohols, for example glycerin, glycols and/or polyethyleneglycol, as moisture-retaining agents for reducing evaporation, and fat-restoring substances, such as fatty acid esters with low polyethyleneglycols, that is to say lipophilic substances soluble in aqueous mixture as a replacement for the fatty substances removed from the skin by the ethanol, and, if necessary, other adjuncts and additives.

The manufacture of the topically administrable pharmaceutical preparations is carried out in a manner known per se, for example by dissolving or suspending the active substance in the base material or in a portion thereof, if necessary. When processing the active substance in the form of a solution, this is usually dissolved in one of the two phases before emulsification; when processing in the form of a suspension, it is usually mixed with a portion of the base after emulsification and then added to the rest of the formulation.

The present invention relates also to the use of compounds of the formula I and the salts of such compounds with salt-forming properties preferably for the treatment of inflammations, especially inflammatory disorders of the rheumatic type, especially chronic arthritis.

The following examples illustrate the above-described invention but are not intended in any way to limit the scope thereof. Temperatures are in degrees Centigrade.

There is no consistent characterisation in the literature of the linking points in the pyrimido-indole ring system,

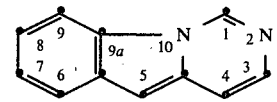

forming the basis of the compounds of the formula I.

Thus, the older literature sources characterise the linking points in the ring system by [3,4-a], whereas recently the characterisation [1,6-a] has been used.

From considerations of principle, the following nomenclature is used hereinafter for the above ring structure: pyrimido[1,6-a]indole.

Example 1:
7-(methoxy-1-(p-chlorophenyl)-3,4-dihydropyrimido[1,6-a]indole-5-acetic acid ethyl ester hydrochloride 165 g (0.4 mol) of 2-[(p-chlorobenzoyl-amino)-ethyl]-5-methoxy-indole-3-acetic acid ethyl ester are boiled under reflux for 3 hours in 825 ml of phosphorus trichloride and excess phosphorus trichloride is subsequently distilled off at a bath temperature of 60° under a slight vacuum. The residue is dissolved in 1500 ml of methylene chloride, extracted by stirring with 2000 ml of ice-water and rendered alkaline by adding 500 ml of concentrated ammonia and, after brief stirring, the methylene chloride phase is separated off. The methylene chloride phase is washed neutral with water, dried over Na$_2$SO$_4$ and the methylene chloride is distilled off. The residue (136.7 g) is dissolved in 120 ml of acetone and 500 ml of ether, and 100 ml of an approximately 4 normal hydrogen chloride solution in ether are added to the solution. While so doing, the hydrochloride of 7-methoxy-1-(p-chlorophenyl-3,4-dihydro-pyrimido[1,6-a]indole-acetic acid ethyl ester crystallises out.

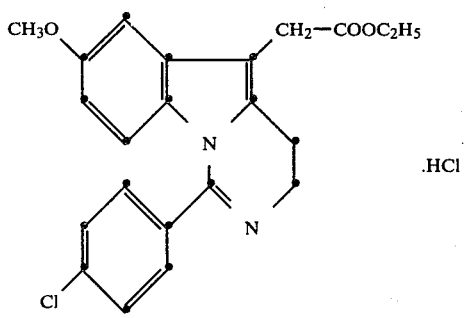

The latter is filtered with suction and washed with acetone/ether 1:10 yielding yellowish crystals having a melting point of 204°–208° and, after recrystallisation from methanol/acetone; a melting point of 205°–208°.

The starting material can be manufactured as follows:

(a) 131 g (0.45 mol) of 3-benzyl-6-methoxy-tetrahydro-γ-carboline are dissolved at 40°, while stirring, in 1300 ml of acetonitrile, and, in the course of 10 minutes, 94 g (0.55 mol) of benzyl bromide are added. After a short time, the benzyl ammonium derivative begins to crystallise out. Stirring is continued at room temperature for approximately 15 hours, the mixture is then cooled in an ice bath, and the crystals are filtered with suction; m.p. 150°–151°.

(b) 464 g (1 mol) of the resulting N,N-dibenzyl-6-methoxy-tetrahydro-γ-carboliminium bromide are dissolved, while heating to 65°, in 4250 ml of methanol, and, in the course of 5 minutes and while stirring, a solution of 196 g (4 mol) of sodium cyanide in 500 ml of water is added. The solution is boiled under reflux for 3 hours. On cooling, 2-(dibenzylamino-ethyl)-3-cyanomethyl-5-methoxy-indole crystallises, after seeding, to yield colourless crystals having a melting point of 102°–104°.

(c) 220 g (0.537 mol) of the nitrile produced in (b) are dissolved in 300 ml of absolute ethanol and the solution is saturated, at −5°, with dry hydrogen chloride. The solution is then stirred for 5½ days at 20°. The separated crystals are allowed to settle, the supernatant solution is decanted, the sediment is dissolved in 2000 ml of ice-water and the solution is stirred for approximately 3 hours at 20°. While cooling with ice, it is then rendered alkaline with concentrated ammonia solution and extracted by stirring with 1500 ml of toluene/ice-water. The separated toluene phase is washed with water, dried over sodium sulphate and filtered over 1000 g of aluminium oxide (Act. Grade 3) and subsequently washed with toluene. After distilling off the toluene, a light brown oil remains which is subjected to hydrogenation as described in (d) without further purification.

(d) 181.3 g of the 2-dibenzylamino-5-methoxy-indole-3-acetic acid ethyl ester obtained in (c) are dissolved in 1500 ml of absolute alcohol and hydrogenated at 20°–35° under normal pressure with the addition of 18 g of palladium-on-carbon (5%). When 12500 ml of H$_2$ have been absorbed a further 18 g of catalyst are added and hydrogenation is continued until the absorption of H$_2$ ceases at a total of 17300 ml. After filtering off the catalyst and subsequently washing with methylene chloride, the solution is concentrated to dryness by evaporation and the residue is dissolved in 250 ml of ether. After seeding, 2-aminoethyl-5-methoxy-indole-3-acetic acid ethyl ester crystallises to form colourless crystals having a melting point of 79°–80°.

(e) 61.7 g (0.223 mol) of the 2-aminoethyl-5-methoxy-indole-3-acetic acid ethyl ester produced in (d) are dissolved in 600 ml of methylene chloride and the solution is covered with a layer of 150 ml of 2 N sodium hydroxide solution. A solution of 43 g (0.245 mol) of p-chlorobenzoyl chloride is added, at 0°–5°, in the course of 2½ hours, while stirring vigorously, and extraction by stirring is then carried out for a further hour. The methylene chloride phase is then separated off, washed with water, dried over MgSO$_4$ and concentrated to dryness by evaporation. The residue crystallises on being taken up in ether, to form colourless crystals of 2-[(p-chlorobenzoyl-amino)-ethyl]-5-methoxy-indole-3-acetic acid ethyl ester having a melting point of 136°–138°.

Example 2:
1-Phenyl-3,4-dihydro-pyrimido[1,6-a]indole-5-acetic acid ethyl ester 54 g (0.154 mol) of 2-(benzoylamino-ethyl)-indole-3-acetic acid ethyl ester are boiled under reflux for 3 hours in 250 ml of phosphorus oxychloride. Excess phosphorus oxychloride is then distilled off at 60° in vacuo and the residue is stirred with 1000 ml of ice-water. The aqueous solution is clarified by filtration over Hyflo, rendered alkaline with concentrated ammonia and extracted with 500 ml of ether. The ether phase is dried over sodium sulphate and concentrated to dryness. The residue is dissolved in 200 ml of acetone, and 25 ml of an approximately 4 normal hydrogen chloride solution in ether are added. After seeding, the hydrochloride of 1-phenyl-3,4-dihydro-pyrimido[1,6-a]indole-5-acetic acid ethyl ester crystallises to form yellowish crystals having a melting point of 172°–175°, which can be recrystallised from 1 N hydrochloric acid (melting point 187°–189°). The base liberated from the salt melts at 83°–84° after recrystallisation from ether.

The 2-(benzoylamino-ethyl)-indole-3-acetic acid ethyl ester having a melting point of 162°–163° which is used as starting material can be manufactured analogously to Example 1 a–e.

Example 3

7-fluoro-1-(p-methylthio-phenyl)-3,4-dihydro-pyrimido[1,6-a]indole-5-acetic acid ethyl ester having a melting point of 119°–120° is obtained, in a manner analogous to that described in Example 2, from 2-[(p-methylthio-benzoyl-amino)-ethyl]-5-fluoro-indole-acetic acid ethyl ester having a melting point of 157°–158°.

Example 4

6,8-dimethyl-1-phenyl-3,4-dihydro-pyrimido[1,6-a]indole-5-acetic acid ethyl ester having a melting point of 142°–143° is obtained, in an analogous manner, from 2-benzoyl-aminoethyl-4,5-dimethyl-indole-3-acetic acid ethyl ester having a melting point of 183°–184°.

Example 5

1-(3-sulphamoyl-4-chloro-phenyl)-3,4-dihydro-pyrimido[1,6-a]indole-5-acetic acid ethyl ester having a melting point of 227°–228° is obtained, in an analogous manner, from 2-[(3-sulphamoyl-4-chlorobenzoyl-amino)-ethyl]-indole-3-acetic acid ethyl ester having a melting point of 212°–213°.

Example 6

1-(2,6-dichlorophenyl)-3,4-dihydro-pyrimido[1,6-a]indole-5-acetic acid ethyl ester having a melting point of 92°–93° (hydrochloride m.p. 138°–142°) is obtained, in an analogous manner, from 2-(2,6-dichlorobenzoyl-aminoethyl)-indole-3-acetic acid ethyl ester having a melting point of 125°–126°.

Example 7

1-(2-picolinyl)-3,4-dihydro-pyrimido[1,6-a]indole-5-acetic acid ethyl ester having a melting point of 113°–114° (hydrochloride m.p. 192°–204°) is obtained, in an analogous manner, from 2-(2-picolinoyl)-aminoethyl)-indole-3-acetic acid ethyl ester having a melting point of 117°–118°.

Example 8

The hydrochloride of 1-(2-thienyl)-3,4-dihydro-pyrimido[1,6-a]indole-5-acetic acid ethyl ester having a melting point of 153°–157° is obtained, in an analogous manner, from 2-(2-thienylamino-ethyl)-indole-3-acetic acid ethyl ester having a melting point of 140°–141°.

Example 9:
7-methoxy-1-(p-chlorophenyl)-3,4-dihydro-pyrimido[1,6-a]indole-5-acetic acid 117.2 g (0.27 mol) of 7-methoxy-1-(p-chlorophenyl)-3,4-dihydro-pyrimido[1,6-a]indole-5-acetic acid ethyl ester hydrochloride are introduced, while stirring, into a solution of 550 g of potassium hydroxide in 200 ml of water and 1500 ml of methanol. The mixture is stirred for 10 hours at room temperature, the methanol is distilled off in vacuo, the residue is dissolved in 1500 ml of ice-water, and 700 ml of concentrated hydrochloric acid are added to the solution while cooling with ice. The separated hydrochloride is filtered with suction and recrystallised from 2300 ml of 50% ethanol to yield 7-methoxy-1-(p-chlorophenyl)-3,4-dihydro-pyrimido[1,6-a]indole-5-acetic acid hydrochloride in the form of yellowish crystals having a melting point of 225°–228° (with decomposition).

Example 10

The hydrochloride of 1-phenyl-3,4-dihydro-pyrimido[1,6-a]indole-5-acetic acid having a melting point of 235°–240° (with decomposition) is obtained in an analogous manner from the corresponding ethyl ester.

Example 11

The hydrochloride of 7-fluoro-1-(p-methylthio-phenyl)-3,4-dihydro-pyrimido[1,6-a]indole-5-acetic acid having a melting point of 220°–222° (with decomposition) is obtained in an analogous manner from the corresponding ethyl ester.

Example 12

The hydrochloride of 7-fluoro-1-(p-methylsulphinyl-phenyl)-3,4-dihydro-pyrimido[1,6-a]indole-5-acetic acid having a melting point of 208°–210° (with decomposition) is obtained in an analogous manner from the corresponding ethyl ester.

Example 13

The hydrochloride of 6,8-dimethyl-1-phenyl-3,4-dihydro-pyrimido[1,6-a]indole-5-acetic acid having a melting point of 212°–220° (with decomposition) is obtained in an analogous manner from the corresponding ethyl ester. The corresponding hemihydrate has a melting point of above 210°.

Example 14

The hydrochloride of 1-(3-sulphamoyl-4-chloro-phenyl)-3,4-dihydro-pyrimido[1,6-a]indole-5-acetic acid having a melting point of 216°–220° (with decomposition) is obtained in an analogous manner from the corresponding ethyl ester.

Example 15

The hydrochloride of 1-(2,6-dichlorophenyl)-3,4-dihydro-pyrimido[1,6-a]indole-5-acetic acid having a melting point of 270°–277° (with decomposition) is obtained in an analogous manner from the corresponding ethyl ester.

Example 16

The hydrochloride of 1-(2-thienyl)-3,4-dihydro-pyrimido[1,6-a]indole-5-acetic acid having a melting point of 203°–235° (with decomposition) is obtained in an analogous manner from the corresponding ethyl ester. 1-(2-thienyl)-3,4-dihydro-pyrimido[1,6-a]indole-5-acetic acid crystallises at pH 6–7 from the aqueous solution of the hydrochloride, in the form of an internal salt having a melting point of 187°–189°.

Example 17:
1-phenyl-3,4-dihydro-pyrimido[1,6-a]indole-5-acetic acid amide 1 g (0.003 mol) of 1-phenyl-3,4-dihydro-pyrimido[1,6-a]indole-5-acetonitrile is heated at 100° for 30 minutes in 10 g of polyphosphoric acid. The reaction mixture is dissolved in 100 ml of water, the solution is rendered alkaline, while cooling with ice, by adding concentrated ammonia and the reaction product is extracted with methylene chloride. The methylene chloride phase is washed neutral with water, dried over $Na_2SO_4$ and the solution is concentrated to dryness. The solid 1-phenyl-3,4-dihydro-pyrimido[1,6-a]indole-5-acetic acid amide remaining as residue is recrystallised from methanol to yield colourless crystals having a melting point of 239°–240°. The corresponding hydrochloride has a melting point of 253°–260° (with decomposition).

The starting material can be manufactured as follows:

(a) 38 g (0.1 mol) of 2-(dibenzylamino-ethyl)-indole-3-acetonitrile are introduced into 300 g of polyphosphoric acid and the mixture is heated at 100°, while stirring, for approximately 60 minutes. The mixture is poured onto 1 kg of ice, rendered alkaline by adding concentrated ammonia and extracted with ether. After washing and drying the ether phase and concentrating it by evaporation, 2-(dibenzylamino-ethyl)-indole-3-acetamide is obtained as a syrup which can be crystallised from a little ether; m.p. 135°–136°.

(b) 120 g (0.3 mol) of 2-(dibenzylamino-ethyl)-indole-3-acetamide are hydrogenated at 30°–35° under normal pressure, with the addition of 12 g of 5% palladium-on-carbon, in 1.2 liters of methanol. When 14.4 liters of hydrogen have been absorbed, hydrogenation is discontinued, the catalyst is filtered off and the solution is concentrated to dryness in vacuo. The residue is recrystallised from 100 ml of ethanol with the addition of 250 ml of ether. The resulting 2-aminoethyl-indole-3-acetamide has a melting point of 156°–157°.

(c) 17.5 ml (0.15 mol) of benzoyl chloride are added, while stirring thoroughly and cooling to approximately 5°, to 21.7 g (0.1 mol) of 2-aminoethyl-indole-3-acetamide in a mixture of 200 ml of ether and 100 ml of water, and 100 ml of 2 N NaOH are gradually added dropwise. The reaction is complete after approximately 1 hour. Stirring is continued for 1 hour at 0°–5° and the separated 2-(benzoylamino-ethyl)-indole-3-acetamide having a melting point of 223°–225° is filtered with suction.

(d) 1.6 g (0.005 mol) of 2-(benzoylamino-ethyl)-indole-3-acetamide is heated under reflux for 2 hours in 16 ml of phosphorus oxychloride. Excess phosphorus oxychloride is distilled off, the oily residue is taken up in water and by-products of the reaction are removed by extracting with ether. Concentrated ammonia is added to the aqueous phase, while cooling, and extraction with ether is carried out. After washing and drying the ether phase and concentrating it by evaporation, 1-phenyl-3,4-dihydro-pyrimido[1,6-a]indole-5-acetonitrile is obtained as a yellowish oil which, by dissolving in methanol and adding ethereal hydrochloric acid, can be converted into a crystalline hydrochloride having a melting point of 195°–205°.

Example 18

The hydrochloride of 1-(3-sulphamoyl-4-chloro-phenyl)-3,4-dihydro-pyrimido[1,6-a]indole-5-acetamide having a melting point of 249°–257° (with decomposition) is obtained, in a manner analogous to that described in Example 17, from 1-(3-sulphamoyl-4-chloro-phenyl)-3,4-dihydro-pyrimido[1,6-a]indole-5-acetonitrile having a melting point of 280°–285°.

Example 19

12 g (0.03 mol) of 1-(p-methylthio-phenyl)-3,4-dihydro-pyrimido[1,6-a]indole-5-acetic acid ethyl ester are dissolved in 120 ml of glacial acetic acid, and 4 ml of 30% hydrogen peroxide are added. The mixture is left to stand for approximately 20 hours at room temperature, is poured onto 1 liter of ice-water, rendered alkaline with concentrated ammonia and extracted with ethyl acetate. The ethyl acetate phase is washed, dried and concentrated by evaporation. The resulting 1-(p-methylsulphoxy-phenyl)-3,4-dihydro-pyrimido[1,6-a]indole-5-acetic acid phenyl ester crystallises from ether to yield yellowish crystals having a melting point of 150°–151°.

Example 20

In a manner analogous to that described in Example 1 the hydrochloride of 7-fluoro-1-(p-methylthio-phenyl)-3,4-dihydro-pyrimido[1,6-a]indole-5-acetic acid ethyl ester having a melting point of 210° (with decomposition) is obtained starting from 2-[(p-methylthio-phenyl-amino)ethyl]-5-fluoro-indole-3-acetic acid ethyl ester and, starting from 2-[(p-chloromethylthio-phenyl-amino)ethyl]-5-fluoro-indole-3-acetic acid ethyl ester, there is obtained the hydrochloride of 7-fluoro-1-(p-chloromethylthio-phenyl)-3,4-dihydro-pyrimido[1,6-a]indole-5-acetic acid ethyl ester having a melting point of 198°–202°.

Example 21

The hydrochloride of 7-fluoro-1-(p-methylsulphoxy-phenyl)-3,4-dihydro-pyrimido[1,6-a]indole-5-acetic acid ethyl ester having a melting point of 261°–264° is obtained, in a manner analogous to that described in Example 19, starting from 7-fluoro-1-(p-methylthio-phenyl)-3,4-dihydro-pyrimido[1,6-a]indole-5-acetic acid ethyl ester hydrochloride.

Example 22

7-fluoro-1-(p-methylthio-phenyl)-pyrimido[1,6-a]indole-5-acetic acid having a melting point of 213°–220° (with decomposition) is obtained, in a manner analogous to that described in Example 9, by hydrolysing 7-fluoro-1-(p-methylthio-phenyl)-pyrimido[1,6-a]indole-5-acetic acid ethyl ester.

Example 23:
7-fluoro-1-(p-methylthio-phenyl)-pyrimido-[1,6-a]indole-5-acetic acid ethyl ester 2 g of 7-fluoro-1-(p-methylthio-phenyl)-3,4-dihydro-pyrimido[1,6-a]indole-5-acetic acid ethyl ester are heated under reflux, while stirring, in 20 ml of diphenyl ether with 0.5 g of palladium-on-carbon (10%). After 2 hours, a further 0.5 g of palladium-on-carbon is added and the mixture is heated for a further 3 hours. After filtering off the catalyst, the reaction mixture is concentrated in vacuo, the residue is taken up in a little ethyl acetate and chromatographed over silica gel. Using hexane/ethyl acetate (9:1) fractions are obtained which, after concentration by evaporation and recrystallization from ether, yield 7-fluoro-1-(p-methylthio-phenyl)-pyrimido[1,6-a]indole-5-acetic acid ethyl ester having a melting point of 120°–122°.

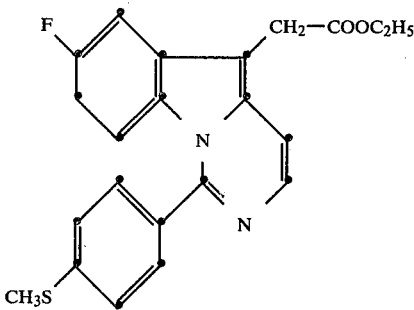

The following are obtained in an analogous manner:
1-phenyl-pyrimido[1,6-a]indole-5-acetic acid ethyl ester having a melting point of 59°–62°
and
7-methoxy-1-(p-chlorophenyl)-pyrimido[1,6-a]indole-5-acetic acid ethyl ester having a melting point of 130°–131°.

Example 24

1.0 g (0.003 mol) of 1-phenyl-3,4-dihydropyrimido[1,6-a]indole-5-acetonitrile is stirred for 48 hours at 0° in 50 ml of absolute ethanol and 50 ml of ethanol saturated with hydrogen chloride. The solvent is then distilled off under reduced pressure. The remaining, crude hydrochloride of 1-phenyl-3,4-dihydro-pyrimido[1,6-a]indole-5-acetiminoethyl ester is suspended in 10 ml of water and heated at 40° for 15 minutes while stirring. After cooling, 1-phenyl-3,4-dihydropyrimido[1,6-a]indole-5-acetic acid ethyl ester hydrochloride crystallises and, after recrystallisation from 1 N hydrochloric acid, yields crystals having a melting point of 187°–189°.

Example 25

3.84 g (0.01 mol) of 7-fluoro-1-(p-methoxysulphoxyphenyl)-3,4-dihydro-pyrimido[1,6-a]indole-5-acetic acid ethyl ester are heated under reflux for 2 hours, while stirring, in 500 ml of ethyl acetate with 40 g of deactivated Raney nickel. The catalyst is then filtered off and the filtrate is concentrated by evaporation under reduced pressure. The residue yields, after recrystallisation from ether, 7-fluoro-1-(p-methylthio-phenyl)-3,4-dihydro-pyrimido[1,6-a]indole-5-acetic acid ethyl ester having a melting point of 119°–120°.

Example 26

38 g of 7-fluoro-1-phenyl-3,4-dihydro-pyrimido[1.6-a]indole-5-acetic acid ethyl ester are heated to 260° C., while stirring in 200 ml of diphenyl ether in the course of 50 minutes. The diphenyl ether is evaporated to dryness under reduced pressure, the residue is taken up in diphenyl ether, the catalyst is filtered off and the solution is concentrated to the beginning of crystallisation. The residue is stirred with hexane and a small portion of diethyl ether and then filtered off. The resulting 7-fluoro-1-phenyl-pyrimido[1,6-a]indole-5-acetic acid ethyl ester melts at 91°–95°.

The starting material can be manufactured as follows:
(a) 131 g (0.45 mol) of 3-benzyl-6-fluoro-tetrahydro-γ-carboline are dissolved at 40°, while stirring, in 1300 ml of acetonitrile, and, in the course of 10 minutes, 94 g (0.55 mol) of benzyl bromide are added. After a short time, the benzyl ammonium derivative begins to crystallise out. Stirring is continued at room temperature for approximately 15 hours, the mixture is then cooled in an ice bath, and the crystals are filtered with suction.
(b) 464 g (1 mol) of the resulting N,N-dibenzyl-6-methoxy-tetrahydro-γ-carboliminium bromide are dissolved, while heating to 65°, in 4250 ml of methanol, and, in the course of 5 minutes and while stirring, a solution of 196 g (4 mol) of sodium cyanide in 500 ml of water is added. The solution is boiled under reflux for 3 hours. On cooling, 2-(dibenzylamino-ethyl)-3-cyanomethyl-methyl-5-fluoro-indole crystallises, after seeding, to yield colourless crystals.
(c) 220 g (0.537 mol) of the nitrile produced in (b) are dissolved in 300 ml of absolute ethanol and the solution is saturated, at −5°, with dry hydrogen chloride. The solution is then stirred for 5½ days at 20°. The separated crystals are allowed to settle, the supernatant solution is decanted, the sediment is dissolved in 2000 ml of ice-water and the solution is stirred for approximately 3 hours at 20°. While cooling with ice, it is then rendered alkaline with concentrated ammonia solution and extracted by stirring with 1500 ml of toluene/ice-water. The separated toluene phase is washed with water, dried over sodium sulphate and filtered over 1000 g of aluminium oxide (Act. Grade 3) and subsequently washed with toluene. After distilling off the toluene, a light brown oil remains which is subjected to hydrogenation as described in (d) without further purification.
(d) 181.3 g of the 2-dibenzylamino-5-fluoro-indole-3-acetic acid ethyl ester obtained in (c) are dissolved in 1500 ml of absolute alcohol and hydrogenated at 20°–35° under normal pressure with the addition of 18 g of palladium-on-carbon (5%). When 12500 ml of $H_2$ have been absorbed a further 18 g of catalyst are added and hydrogenation is continued until the absorption of $H_2$ ceases at a total of 17300 ml. After filtering off the catalyst and subsequently washing with methylene chloride, the solution is concentrated to dryness by evaporation and the residue is dissolved in 250 ml of ether. After seeding, 2-aminoethyl-5-fluoro-indole-3-acetic acid ethyl ester crystallises to form colourless crystals.
(e) 61.7 g (0.223 mol) of the 2-aminoethyl-5-fluoro-indole-3-acetic acid ethyl ester produced in (d) are dissolved in 600 ml of methylene chloride and the solution is covered with a layer of 150 ml of 2 N sodium hydroxide solution. A solution of 43 g (0.245 mol) of benzoyl chloride is added, at 0°–5°, in the course of 2½ hours, while stirring vigorously, and extraction by stirring is then carried out for a further hour. The methylene chloride phase is then separated off, washed with water, dried over $MgSO_4$ and concentrated to dryness by evaporation. The residue crystallises on being taken up in ether, to form colourless crystals of 2-[(benzoyl-amino)-ethyl]-5-fluoro-indole-3-acetic acid ethyl ester.
(f) 165 g (0.4 mol) of 2-[(benzoyl-amino)-ethyl]-5-fluoro-indole-3-acetic acid ethyl ester are boiled under reflux for 3 hours in 825 ml of phosphorus trichloride and excess phosphorus trichloride is subsequently distilled off at a bath temperature of 60° under a slight vacuum. The residue is dissolved in 1500 ml of methylene chloride, extracted by stirring with 2000 ml of ice-water and rendered alkaline by adding 500 ml of concentrated ammonia and, after brief stirring, the methylene chloride phase is separated off. The methylene chloride phase is washed neutral with water, dried over $Na_2SO_4$ and the methylene chloride is distilled off. The residue is dissolved in 120 ml of acetone and 500 ml of ether, and 100 ml of an approximately 4 normal hydrogen chloride solution in ether are added to the solution. While so doing, the hydrochloride of 7-fluoro-1-phenyl-3,4-dihydro-pyrimido[1,6-a]indole-acetic acid ethyl ester crystallises out after seeding. The base liberated from the salt melts, after recrystallization from ether, at 56°–58°.

Example 27

7-fluoro-1-(p-methanesulphinyl-phenyl)-pyrimido[1,6-a]indole-5-acetic acid ethyl ester, m.p. 133°–135°, is obtained, in a manner analogous to that described in Example 26, starting from 2-amino-ethyl-5-fluoro-indole-3-acetic acid ethyl ester and p-methanesulphinyl-benzoyl chloride and the resulting 7-fluoro-1-(p-methanesulphinyl-phenyl)-3,4-dihydro-pyrimido[1,6-a]indole-5-acetic acid ethyl ester (m.p. of the hydrochloride 208°–210°).

Example 28

1-(2-thienyl)-pyrimido[1,6-a]indole-5-acetic acid ethyl ester, m.p. 94°–95°, is obtained, in a manner analogous to that described in Example 26, starting from 2-aminoethyl-indole-3-acetic acid ethyl ester and 2- thenoyl chloride and the resulting 1-(2-thienyl)-3,4-dihydro-pyrimido[1,6-a]indole-5-acetic acid ethyl ester (m.p. of the hydrochloride 153°–157°).

Example 29

7-methoxy-1-(2-picolinyl)-pyrimido[1,6-a]indole-5-acetic acid ethyl ester, m.p. 103°–104°, is obtained, in a manner analogous to that described in Example 26, starting from 2-aminoethyl-5-methoxy-indole-3-acetic acid ethyl ester and 2-picolyl chloride and the resulting 7-methoxy-1-(2-picolinyl)-3,4-dihydro-pyrimido[1,6-a]indole-5-acetic acid ethyl ester.

Example 30

12,2 g of 1-phenyl-pyrimido[1,6-a]indole-5-acetic acid ethyl ester (m.p. 59°–62°), obtained from 2-aminoethyl-indole-3-acetic acid ethyl ester and benzoylchloride and the resulting 1-phenyl-3,4-dihydro-pyrimido[1,6-a]indole-5-acetic acid ethyl ester (m.p. 83°–84°), are stirred with 30 ml of ethanol and 40 ml of 2n sodium hydroxide in the course of 3 hours at room temperature. The mixture is acidified with concentrated hydrochloric acid to pH=3 and 30 ml of propyleneoxide, while stirring, are added. After short time 1-phenyl-pyrimido[1,6-a]indole-5-acetic acid crystallises out and is filtered off. The acid is recrystallised from ethanol, m.p. 198–204 (decomposition).

Example 31

7-fluoro-1-(p-methylthio-phenyl)-pyrimido[1,6-a]indole-5-acetic acid, m.p. 201°–206° (decomposition), is obtained, in a manner analogous to that described in Example 30, starting from 2-aminoethyl-5-fluoro-indole-3-acetic acid ethyl ester and the resulting 7-fluoro-1-(p-methylthio-phenyl)-3,4-dihydro-pyrimido[1,6-a]indole-5-acetic acid ethyl ester, m.p. 119°–120°.

Example 32

In a manner analogous to that described in Example 30, 7-fluoro-1-(p-methanesulphinylphenyl)-pyrimido[1,6-a]indole-5-acetic acid, m.p. 218°–224° (decomposition), is obtained starting from 7-fluoro-1-(p-methanesulphinyl-phenyl)-pyrimido[1,6-a]indole-5-acetic acid ethyl ester.

Example 33

In a manner analogous to that described in Example 30, 7-fluoro-1-phenyl-pyrimido[1,6-a]indole-5-acetic acid, m.p. 217°–220°, is obtained starting from 7-fluoro-1-phenyl-pyrimido[1,6-a]indole-5-acetic acid ethyl ester.

Example 34

In a manner analogous to that described in Example 30, 1-(2-thienyl)-pyrimido[1,6-a]indole-5-acetic acid, m.p. 196°–200° (decomposition), is obtained starting from 1-(2-thienyl)-pyrimido[1,6-a]indole-5-acetic acid ethyl ester.

Example 35

In a manner analogous to that described in Example 32, 7-methoxy-1-(2-picolinyl)-pyrimido[1,6-a]indole-5-acetic acid, m.p. 201°–206°, is obtained, starting from 7-methoxy-1-(2-picolinyl)-pyrimido[1,6-a]indole-5-acetic acid ethyl ester.

Example 36

In a manner analogous to that described in Example 26 and 30, the following compounds are obtained:
7-fluoro-1-(p-methoxyphenyl)-pyrimido[1,6-a]indole-5-acetic acid, m.p. 220°–225°, and the ethyl ester thereof,
7-methoxy-1-(p-fluorophenyl)-pyrimido[1,6-a]indole-5-acetic and the ethyl ester thereof, and
7-fluoro-1-(2-thienyl)-pyrimido[1,6-a]indole-5-acetic acid, m.p. 233°–236°.

Example 37

3 g of 7-fluoro-1-phenyl-3,4-dihydro-pyrimido[1,6-a]indole-5-acetic acid ethyl ester are heated to reflux, while stirring, with 1 g of selenium dioxide in 50 ml of chlorobenzene and 5 ml of glacial acetic acid in the course of 1.5 hours. The mixture is evaporated to dryness, the residue is dissolved in 20 ml of acetic acid ethyl ester, the selenium is filtered off, the solution is washed with sodium bicarbonate to neutral reaction and evaporated to dryness. The residue is dissolved in ether and chromatographed over silica gel. 7-fluoro-1-phenyl-pyrimido[1,6-a]indole-5-acetic acid ethyl ester is eluted with hexane/acetic acid ethyl ester (4:1) and recrystallised from ether/hexane, m.p. 91°–93°.

Example 38

To a solution of 3.38 g of 1-(2-thienyl)-3,4-dihydro-pyrimido[1,6-a]indole-5-acetic acid ethyl ester in 20 ml of dimethoxyethane in the course of 0.5 hours a solution of 0.01 mole diphenylselenium-bis-(trifluoroacetate) (manufactured according to J. Amer. Chem. Soc. 103, 4643 (1981)). The mixture is kept for 3 hours at room temperature, evaporated to dryness. The residue is dissolved in ether, washed with sodium bicarbonate and chromatographed over 80 g of silica gel. The resulting 1-(2-thienyl)-pyrimido[1,6-a]indole-5-acetic acid ethyl ester is eluted with hexane/acetic acid ethyl ester (4:1) and recrystallised from ether/hexane in yellow crystals, m.p. 94°–95°.

Example 39

Tablets each containing 25 mg of active substance, for example 7-fluoro-1-(p-methylthio-phenyl)-3,4-dihydro-pyrimido[1,6-a]indole-5-acetic acid or a salt thereof, for example the hydrochloride, can be manufactured in the following manner:

| Constituents (for 1000 tablets): | |
|---|---|
| active substance | 25.0 g |
| lactose | 100.7 g |
| wheat starch | 7.5 g |
| polyethylene glycol 6000 | 5.0 g |
| talc | 5.0 g |
| magnesium stearate | 1.8 g |
| demineralised water | q.s. |

Manufacture

All the solid ingredients are first forced through a sieve having a mesh width of 0.6 mm. Then the active substance, lactose, talc, magnesium stearate and half of the starch are mixed. The other half of the starch is suspended in 40 ml of water and this suspension is added to a boiling solution of the polyethylene glycol in 100 ml of water. The resulting starch paste is added to the main portion and the mixture is granulated, if necessary with the addition of water. The granulate is dried overnight at 35°, forced through a sieve having a mesh width of 1.2 mm and pressed to form tablets of approximately 6 mm diameter having concave faces on both sides.

In an analogous manner, it is also possible to manufacture tablets each containing 25 mg of one of the compounds of the formula I mentioned in Examples 1 to 19, it being possible for the compounds to be also in the form of acid addition salts, such as hydrochlorides, and for compounds in which $R_2$ is 1-carboxymethyl to be also in the form of salts and bases, such as sodium, potassium or zinc salts.

Example 40

Tablets for chewing, each containing 30 mg of active substance, for example 7-fluoro-1-(p-methylthiophenyl)-3,4-dihydro-pyrimido[1,6-a]indole-5-acetic acid or a salt thereof, for example the hydrochloride, can be manufactured, for example in the following manner:

| Composition (for 1000 tablets): | |
|---|---|
| active substance | 30.0 g |
| mannitol | 267.0 g |
| lactose | 179.5 g |
| talc | 20.0 g |
| glycine | 12.5 g |
| stearic acid | 10.0 g |
| saccharine | 1.0 g |
| 5% gelatine solution | q.s |

Manufacture

All the solid ingredients are first forced through a sieve having a mesh width of 0.25 mm. The mannitol and the lactose are mixed and granulated with the addition of the gelatine solution, the mixture is forced through a sieve having a mesh width of 2 mm, dried at 50° and again forced through a sieve having a mesh width of 1.7 mm. The active substance, glycine and saccharine are carefully mixed, the mannitol, the lactose granulate, the stearic acid and the talc are added, and the whole is thoroughly mixed and pressed to form tablets of approximately 100 mm diameter having concave faces on both sides and a break groove on the upper side.

In an analogous manner it is also possible to manufacture tablets for chewing, each containing 30 mg of one of the compounds of the formula I mentioned in Examples 1 to 38, it being possible for the compounds to be also in the form of acid addition salts, such as hydrochlorides, and for compounds in which $R_2$ is 1-carboxymethyl to be also in the form of salts with bases, such as sodium, potassium or zinc salts.

Example 41

Tablets each containing 100 mg of active substance, for example 7-fluoro-1-(p-methylthio-phenyl)-3,4-dihydropyrimido[1,6-a]indole-5-acetic acid or a salt thereof, for example the hydrochloride, can be manufactured in the following manner:

| Composition (for 1000 tablets): | |
|---|---|
| active substance | 100.0 g |
| lactose | 248.5 g |
| corn starch | 17.5 g |
| polyethylene glycol 6000 | 5.0 g |
| talc | 15.0 g |
| magnesium stearate | 4.0 g |
| demineralised water | q.s. |

Manufacture

The solid ingredients are first forced through a sieve having a mesh width of 0.6 mm. Then the active substance, lactose, talc, magnesium stearate and half of the starch are intimately mixed. The other half of the starch is suspended in 65 ml of water and this suspension is added to a boiling solution of the polyethylene glycol in 260 ml of water. The resulting paste is added to the pulverulent substances, and the whole is mixed and granulated, if necessary with the addition of water. The granulate is dried overnight at 35°, forced through a sieve having a mesh width of 1.2 mm and pressed to form tablets of approximately 10 mm diameter having concave faces on both sides and a break groove on the upper side.

In an analogous manner, it is also possible to manufacture tablets each containing 100 mg of a compound of the formula I according to Examples 1 to 38, it being possible for compounds to be also in the form of acid addition salts, such as hydrochlorides, and for compounds in which $R_2$ is 1-carboxymethyl to be also in the form of salts with bases, such as sodium, potassium or zinc salts.

What is claimed is:

1. N,N'-bridged carboxylic acid amidines of the general formula

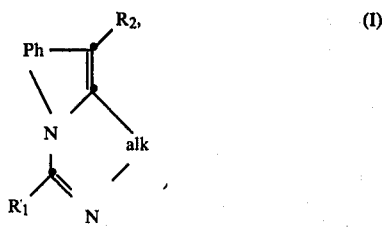

in which $R_1$ represents phenyl optionally mono- or di-substituted by identical or different groups selected from lower alkyl, lower alkoxy, lower alkylthio, halogeno-lower alkylthio, lower alkanesulphinyl, halogeno-lower alkanesulphinyl, lower alkanesulphonyl, halogeno-lower alkanesulphonyl, sulphamoyl, N-mono- or N,N-di-lower alkylsulphamoyl and halogen, or represents pyrrolyl, furyl, thienyl, thiazolyl, pyridyl or pyrimidyl each optionally mono- or di-substituted by identical or different groups selected from lower alkyl, lower alkoxy and halogen, $R_2$ represents a group of the formula —CH($R_3$)—$R_2'$ in which $R_2'$ is carboxy, phenyl- or pyridyl-lower alkoxycarbonyl optionally substituted by lower alkyl, lower alkoxy or halogen, hydroxy- or lower alkoxy-lower alkoxycarbonyl, lower alkoxycarbonyl, carbamoyl, N-hydroxycarbbamoyl, N-aminocarbamoyl, N-mono- or N,N-di-lower alkylcarbamoyl or -hydroxy-lower alkylcarbamoyl, or pyrrolidino-, piperidino-, morpholino-, thiomorpholino-, piperazino-, N-lower alkylpiperazinocarbonyl, $R_3$ represents hydrogen or lower alkyl, Ph represents 1,2-phenylene optionally mono- or di-substituted by identical or different groups selected from lower alkyl, lower alkoxy, halogen and trifluoromethyl, and alk represents lower alkylene separating the methine group from the imino group by 2 carbon atoms or lower alkenylene separating the methine group from the imino group by 2 carbon atoms, and their salts.

2. Compounds of the formula I according to claim 1 in which $R_1$ represents phenyl optionally mono- or di-substituted by identical or different groups selected from lower alkyl having up to and including 4 carbon atoms, by lower alkoxy having up to and including 4 carbon atoms, by halogeno-lower alkylthio having up to and including 4 carbon atoms, by lower alkylthio having up to an including 4 carbon atoms, by halogeno-lower alkanesulphinyl having up to and including 4 carbon atoms, by lower alkanesulphinyl having up to and including 4 carbon atoms, by halogeno-lower alkanesulphonyl, by lower alkanesulphonyl having up to and including 4 carbon atoms, by sulphamoyl, by N-mono- or N,N-di-lower alkanesulphamoyl each having up to and including 4 carbon atoms in the alkyl radical, and by halogen having an atomic number of up to and including 35, or represents pyridyl or thienyl each optionally mono- or di-substituted by identical or different groups selected from lower alkyl having up to and including 4 carbon atoms, by lower alkoxy having up to and including 4 carbon atoms, and by halogen having an atomic number of up to an including 35, $R_2$ represents a group of the formula —CH($R_3$)—$R_2'$ in which $R_2'$ represents carboxy, phenyl- or pyridyl-lower alkoxycarbonyl, optionally substituted by lower alkyl having up to and including 4 carbon atoms, by lower alkoxy having up to and including 4 carbon atoms, or by halogen, lower alkoxycarbonyl, mono- or di-hydroxy-lower alkoxycarbonyl, lower alkoxy-lower alkoxycarbonyl, N-hydroxy- or N-aminocarbamoyl, N-mono- or N,N-di-lower alkylcarbamoyl, or carbamoyl, $R_3$ is hydrogen or lower alkyl having up to and including 4 carbon atoms, Ph is 1,2-phenylene optionally mono- or di-substituted by identical or different groups selected from lower alkyl having up to an including 4 carbon atoms, by lower alkoxy having up to an including 4 carbon atoms, and by halogen having up to and including an atomic number of 35, and alk is 1,2-ethylene, and their salts.

3. Compounds of the formula I according to claim 1 in which $R_1$ represents phenyl optionally mono- or di-substituted by identical or different groups selected from halogen, lower alkylthio, lower alkanesulphinyl, lower alkanesulphonyl, halogeno-lower alkylthio and sulphamoyl, or pyridyl or thienyl, $R_2$ represents a group of the formula —$CH_2$—$R_2'$ in which $R_2'$ represents carboxy, lower alkoxycarbonyl or carbamoyl, Ph represents 1,2-phenylene optionally mono- or di-substituted by identical or different groups selected from lower alkoxy, lower alkyl and halogen, and alk is 1,2-ethylene or vinylene, and their salts.

4. Compounds of the formula I according to claim 1 in which $R_1$ represents phenyl optionally mono- or di-substituted by identical or different groups selected from halogen having an atomic number of up to and including 35, by lower akylthio having up to and including 4 carbon atoms, by lower alkanesulphinyl having up to and including 4 carbon atoms, by halogeno-lower alkylthio having up to an including 4 carbon atoms, and by sulphamoyl, or pyridyl, or thienyl, $R_2$ represents a group of the formula —$CH_2$—$R_2'$ in which $R_2'$ represents carboxy, lower alkoxycarbonyl having up to and including 5 carbon atoms, or carbamoyl, Ph represents 1,2-phenylene optionally mono- or di-substituted by identical or different groups selected from lower alkoxy having up to and including 4 carbon atoms, by lower alkyl having up to an including 4 carbon atoms, and by halogen having an atomic number of up to and including 35, and alk is 1,2-ethylene or vinylene, and their salts.

5. Compounds of the formula I according to claim 1 in which $R_1$ represents phenyl optionally substituted in the p-position by halo-lower alkylthio having up to and including 4 carbon atoms, by lower alkylthio having up to and including 4 carbon atoms, by lower alkanesulphinyl having up to and including 4 carbon atoms, or by halogen having an atomic number of up to and including 35, or in the 3-position by sulphamoyl and, in addition, in the 4-position by halogen having an atomic number of up to and including 35, or pyridyl or thienyl, $R_2$ represents a group of the formula —$CH_2$—$R_2'$ in which $R_2'$ represents carboxy, lower alkoxycarbonyl having up to and including 5 carbon atoms, or carbamoyl, Ph represents 1,2-phenylene optionally substituted in the 4-position in relation to the bonded nitrogen atom by lower alkoxy having up to and including 4 carbon atoms, in the 3- and 5-position by lower alkyl having up to and including 4 carbon atoms, or in the 4-position by halogen having an atomic number of up to and including 35, and alk is 1,2-ethylene or vinylene, and their salts.

6. Compounds of the formula I according to claim 1 in which $R_1$ represents phenyl optionally substituted in the p-position by lower alkylthio having up to and including 4 carbon atoms, by lower alkanesulphinyl having up to and including 4 carbon atoms, or by halogen having an atomic number of up to and including 35, $R_2$ represents lower alkoxycarbonylmethyl, Ph represents 1,2-phenylene optionally mono-substituted in the 4-position in relation to the bonded nitrogen atom by lower alkoxy having up to and including 4 carbon atoms, or in the 4-position by halogen having an atomic number of up to and including 35, and alk is 1,2-ethylene, and their salts.

7. Compounds of the formula I according to claim 1 in which $R_1$ represents phenyl optionally substituted in the p-position by lower alkylthio having up to and including 4 carbon atoms, by lower alkanesulphinyl having up to and including 4 carbon atoms, or by halogen having up to and including an atomic number of 35, $R_2$ represents carboxymethyl, Ph represents 1,2-phenylene optionally substituted in the p-position to the nitrogen atom by lower alkoxy having up to and including 4 carbon atoms or by halogen having up to and including an atomic number of 35, and alk represents 1,2-ethylene, and their salts.

8. A compound of the formula I according to claim 1 being 7-(methoxy-1-(p-chlorophenyl)-3,4-dihydro-pyrimido[1,6-a]indole-5-acetic acid ethyl ester or a pharmaceutically acceptable salt thereof.

9. A compound of the formula I according to claim 1 being 1-phenyl-3,4-dihydro-pyrimido[1,6-a]indole-5-acetic acid ethyl ester or a pharmaceutically acceptable salt thereof.

10. A compound of the formula I according to claim 1 being 7-fluoro-1-(p-methylthio-phenyl)-3,4-dihydro-pyrimido[1,6-a]indole-5-acetic acid ethyl ester or a pharmaceutically acceptable salt thereof.

11. A compound of the formula I according to claim 1 being 6,8-dimethyl-1-phenyl-3,4-dihydropyrimido[1,6-a]indole-5-acetic acid ethyl ester or a pharmaceutically acceptable salt thereof.

12. A compound of the formula I according to claim 1 being 1-(3-sulphamoyl-4-chloro-phenyl)-3,4-dihydro-pyrimido[1,6-a]indole-5-acetic acid ethyl ester or a pharmaceutically acceptable salt thereof.

13. A compound of the formula I according to claim 1 being 1-(2,6-dichlorophenyl)-3,4-dihydro-pyrimido[1,6-a]indole-5-acetic acid ethyl ester or a pharmaceutically acceptable salt thereof.

14. A compound of the formula I according to claim 1 being 1-(2-picolinyl)-3,4-dihydro-pyrimido[1,6-a]indole-5-acetic acid ethyl ester or a pharmaceutically acceptable salt thereof.

15. A compound of the formula I according to claim 1 being 1-(2-thienyl)-3,4-dihydro-pyrimido[1,6-a]indole-5-acetic acid ethyl ester or a pharmaceutically acceptable salt thereof.

16. A compound of the formula I according to claim 1 being 7-methoxy-1-(p-chlorophenyl)-3,4-dihydro-pyrimido[1,6-a]indole-5-acetic acid or a pharmaceutically acceptable salt thereof.

17. A compound of the formula I according to claim 1 being 1-phenyl-3,4-dihydro-pyrimido[1,6-a]indole-5-acetic acid or a pharmaceutically acceptable salt thereof.

18. A compound of the formula I according to claim 1 being 7-fluoro-1-(p-methylthiophenyl)-3,4-dihydro-pyrimido[1,6-a]indole-5-acetic acid or a pharmaceutically acceptable salt thereof.

19. A compound of the formula I according to claim 1 being 7-fluoro-1-(p-methylsulphinylphenyl)-3,4-dihydro-pyrimido[1,6-a]indole-5-acetic acid or a pharmaceutically acceptable salt thereof.

20. A compound of the formula I according to claim 1 being 6,8-dimethyl-1-phenyl-3,4-dihydro-pyrimido[1,6-a]indole-5-acetic acid or a pharmaceutically acceptable salt thereof.

21. A compound of the formula I according to claim 1 being 1-(3-sulphamoyl-4-chlorophenyl)-3,4-dihydro-pyrimido[1,6-a]indole-5-acetic acid or a pharmaceutically acceptable salt thereof.

22. A compound of the formula I according to claim 1 being 1-(2,6-dichlorophenyl)-3,4-dihydro-pyrimido[1,6-a]indole-5-acetic acid or a pharmaceutically acceptable salt thereof.

23. A compound of the formula I according to claim 1 being 1-(2-thienyl)-3,4-dihydro-pyrimido[1,6-a]indole-5-acetic acid or a pharmaceutically acceptable salt thereof.

24. A compound of the formula I according to claim 1 being 1-phenyl-3,4-dihydro-pyrimido[1,6-a]indole-5-acetic acid amide or a pharmaceutically acceptable salt thereof.

25. A compound of the formula I according to claim 1 being 1-(3-sulphamoyl-4-chlorophenyl)-3,4-dihydro-pyrimido[1,6-a]indole-5-acetamide or a pharmaceutically acceptable salt thereof.

26. A compound of the formula I according to claim 1 being 1-(p-methylsulphoxy-phenyl)-3,4-dihydro-pyrimido[1,6-a]indole-5-acetic acid ethyl ester or a pharmaceutically acceptable salt thereof.

27. A compound of the formula I according to claim 1 being 7-fluoro-1-(p-chloromethylthio-phenyl)-3,4-dihydro-pyrimido[1,6-a]indole-5-acetic acid ethyl ester or a pharmaceutically acceptable salt thereof.

28. A compound of the formula I according to claim 1 being 7-fluoro-1-(p-methoxysulphoxy-phenyl)-3,4-dihydro-pyrimido[1,6-a]indole-5-acetic acid ethyl ester or a pharmaceutically acceptable salt thereof.

29. A compound of the formula I according to claim 1 being 7-fluoro-1-(p-methylthio-phenyl)-pyrimido[1,6-a]indole-5-acetic acid or a pharmaceutically acceptable salt thereof.

30. A compound of the formula I according to claim 1 being 1-phenyl-pyrimido[1,6-a]indole-5-acetic acid ethyl ester or a pharmaceutically acceptable salt thereof.

31. A compound of the formula I according to claim 1 being 7-methoxy-1-(p-chlorophenyl)-pyrimido[1,6-a]indole-5-acetic acid ethyl ester or a pharmaceutically acceptable salt thereof.

32. A compound of the formula I according to claim 1 being 7-fluoro-1-phenyl-pyrimido[1,6-a]indole-5-acetic acid ethyl ester or a pharmaceutically acceptable salt thereof.

33. A compound of the formula I according to claim 1 being 7-fluoro-1-(p-methanesulphinyl-phenyl)-pyrimido[1,6-a]indole-5-acetic acid ethyl ester or a pharmaceutically acceptable salt thereof.

34. A compound of the formula I according to claim 1 being 1-(2-thienyl)-pyrimido[1,6-a]indole-5-acetic acid ethyl ester or a pharmaceutically acceptable salt thereof.

35. A compound of the formula I according to claim 1 being 7-methoxy-1-(2-picolinyl)-pyrimido[1,6-a]indole-5-acetic acid ethyl ester or a pharmaceutically acceptable salt thereof.

36. A compound of the formula I according to claim 1 being 1-phenyl-pyrimido[1,6-a]indole-5-acetic acid or a pharamaceutically acceptable salt thereof.

37. A compound of the formula I according to claim 1 being 7-fluoro-1-(p-methanesulphinyl-phenyl)-pyrimido[1,6-a]indole-5-acetic acid or a pharmaceutically acceptable salt thereof.

38. A compound of the formula I according to claim 1 being 7-fluoro-1-phenyl-pyrimido[1,6-a]indole-5-acetic acid or a pharmaceutically acceptable salt thereof.

39. A compound of the formula I according to claim 1 being 1-(2-thienyl)-pyrimido[1,6-a]indole-5-acetic acid or a pharmaceutically acceptable salt thereof.

40. A compound of the formula I according to claim 1 being 1-(2-thienyl)-pyrimido[1,6-a]indole-5-acetic acid ethyl ester or a pharmaceutically acceptable salt thereof.

41. A compound of the formula I according to claim 1 being 7-methoxy-1-(2-picolinyl)-pyrimido[1,6-a]indole-5-acetic acid or a pharmaceutically acceptable salt thereof.

42. A compound of the formula I according to claim 1 being 7-methoxy-1-(2-picolinyl)-pyrimido[1,6-a]indole-5-acetic acid ethyl ester or a pharmaceutically acceptable salt thereof.

43. A compound of the formula I according to claim 1 being 7-fluoro-1-(p-methoxyphenyl)-pyrimido[1,6-a]indole-5-acetic acid or a pharmaceutically acceptable salt thereof.

44. A compound of the formula I according to claim 1 being 7-methoxy-1-(p-fluorophenyl)-pyrimido[1,6-a]indole-5-acetic acid or a pharmaceutically acceptable salt thereof.

45. A pharmaceutical preparation comprising an analgesic or anti-inflammatory amount of a compound according to claim 1 and a pharmaceutically acceptable carrier.

46. A method of treating inflammation in warm blooded animals comprising administering to an animal in need of such administration an anti-inflammatory effective amount of a compound according to claim 1.

47. A method of treating pain in warm blooded animals comprising administering to an animal in need of such administration an analgisically effective amount of a compound according to claim 1.

* * * * *